US010920240B2

(12) United States Patent
Gautier et al.

(10) Patent No.: US 10,920,240 B2
(45) Date of Patent: Feb. 16, 2021

(54) METHODS AND COMPOSITIONS FOR THE CONTROL OF RUST FUNGI BY INHIBITING EXPRESSION OF THE HXT1 GENE

(71) Applicants: BASF AGRICULTURAL SOLUTIONS SEED, US LLC, Research Triangle Park, NC (US); UNIVERSITY OF HOHENHEIM, Stuttgart (DE)

(72) Inventors: Pierrick Gautier, Reyrieux (FR); Tobias Link, Stuttgart (DE); Manuel Mueller, Pfullingen (DE); Stéphane Peyrard, Craponne (FR); Ralf Voegele, Vaterstetten (DE)

(73) Assignees: BASF AGRICULTURAL SOLUTIONS SEED, US LLC, Research Triangle Park, NC (US); UNIVERSITY OF HOHENHEIM, Stuttgart (DE)

( * ) Notice: Subject to any disclaimer, the term of this patent is extended or adjusted under 35 U.S.C. 154(b) by 0 days.

(21) Appl. No.: 15/748,433

(22) PCT Filed: Jul. 21, 2016

(86) PCT No.: PCT/EP2016/067363
§ 371 (c)(1),
(2) Date: Jan. 29, 2018

(87) PCT Pub. No.: WO2017/016963
PCT Pub. Date: Feb. 2, 2017

(65) Prior Publication Data
US 2018/0298398 A1    Oct. 18, 2018

(30) Foreign Application Priority Data
Jul. 30, 2015    (EP) .................... 15290196

(51) Int. Cl.
*C12N 15/82* (2006.01)
*C07K 14/37* (2006.01)

(52) U.S. Cl.
CPC .......... *C12N 15/8282* (2013.01); *C07K 14/37* (2013.01)

(58) Field of Classification Search
None
See application file for complete search history.

(56) References Cited

U.S. PATENT DOCUMENTS

| | | | | |
|---|---|---|---|---|
| 8,603,788 | B2 * | 12/2013 | Donaldson ............. | C12N 15/01 435/165 |
| 8,927,515 | B2 | 1/2015 | Brown et al. | |
| 2006/0095987 | A1 * | 5/2006 | Niblett ............... | C12N 15/8218 800/279 |
| 2008/0113351 | A1 | 5/2008 | Naito et al. | |
| 2011/0054005 | A1 | 3/2011 | Naito et al. | |
| 2011/0061128 | A1 * | 3/2011 | Roberts ............. | C12N 15/8282 800/279 |

FOREIGN PATENT DOCUMENTS

| | | |
|---|---|---|
| EP | 1752536 A1 | 2/2007 |
| EP | 2213738 A2 | 8/2010 |
| WO | WO 2004/045543 A2 | 6/2004 |
| WO | 2005071091 A1 | 8/2005 |
| WO | WO 2005/116204 A1 | 12/2005 |
| WO | WO 2011/069953 A1 | 6/2011 |
| WO | WO 2012/006241 A2 | 1/2012 |
| WO | WO 2013/040057 A1 | 3/2013 |

OTHER PUBLICATIONS

NCBI Reference Sequence: NM_001179222.2. *Saccharomyces cerevisiae* S288c Hxt4p (HXT4), mRNA. pp. 1-2.*
Voegele et al. The role of haustoria in sugar supply during infection of broad bean by the rust fungus Uromyces fabae. PNAS. 2001. 98(14):8133-8138.*
Yin et al. Development of a host0induced RNAi system in the Wheat Stripe Rust Fungus *Puccinia striiformis* f. sp. *tritici*. Molecular Plant Microbe Interactions. 2011. 24(5):554-561.*
Bork. Go hunting in sequence databases but watch out for traps. TIG. 1996. 12(10): 425-427.*
Brenner. Errors in genome annotation. TIG. 1999. 15(4): 132-133.*
Doerks. Protein Annotation: detective work for function prediction. TIG. 1998. 14(6): 248-250.*
Friedberg. Automated protein function prediction—the genomic challenge. Briefings in Bioinformatics. 2006. 7(3): 225-242.*
GenBank Accession No. FW830919.1, "WO 2005116204-A/237445: Double strand polynucleotides generating RNA interference," last updated date Apr. 18, 2011 (1 page).
GenBank Accession No. HH002232.1, "Sequence 878947 from Patent EP2213738," https://www.ebi.ac.uk/cgi-bin/sva/sva.pl?session=%2Ftmp%2FSESSION22360-1516658129-1&index=0& last updated date Aug. 26, 2010 (1 page).
GenBank Accession No. HK350994.1, "Sequence 3802 from U.S. Pat. No. 8,927,515," https://www.ncbi.nlm.nih.gov/nuccore/914811830, last updated date Aug. 12, 2015 (1 page).
International Search Report issued in International Application No. PCT/EP2016/067363, dated Oct. 27, 2016 (4 pages).
Müller et al., "Etablierung eines Wirts-induzierten RNA-i-Systems für die Kontrolle des Asiatischen Sojabohnenrostes Phakopsora pachyrhizi," 2015, pp. 1-132.
Panwar et al., "Endogenous silencing of Puccinia triticina pathogenicity genes through in planta-expressed sequences leads to the suppression of rust diseases on wheat," The Plant Journal, 2012, pp. 1-12.

(Continued)

*Primary Examiner* — Ashley K Buran
(74) *Attorney, Agent, or Firm* — Arent Fox LLP

(57) ABSTRACT

The present invention relates to methods and compositions for the control of plant fungal pathogens, particularly rusts, by inhibiting one or more biological functions of such plant fungal pathogens, particularly by inhibiting a fungal HXT1 gene using RNA interference (RNAi).

19 Claims, 3 Drawing Sheets

Specification includes a Sequence Listing.

(56) References Cited

OTHER PUBLICATIONS

Panwar et al., "Host-induced gene silencing of wheat leaf rust fungus Puccinia triticina pathogenicity genes mediated by the Barley stripe mosaic virus," Plant Mol. Biol., 2013, pp. 1-14.

Voegele et al., "The role of haustoria in sugar supply during infection of broad bean by the rust fungus Uromyces fabae," PNAS, vol. 98(14), Jul. 2001, pp. 8133-8138.

Yin et al., "Development of a Host-Induced RNAi System in the Wheat Stripe Rust Fungus *Puccinia striiformis* f. sp. *tritici*," MPMI, vol. 24(5), 2011, pp. 554-561.

"Human AR gene transcript targeted Dsi RNA sense strand, SEQ ID 3802", Database Geneseq [Online], May 7, 2015., XP002753214, Database accession No. BBV69656.

European Search Report for EP Patent Application No. 15290196.3, dated Feb. 5, 2016, 8 pages.

International Search Report for PCT Patent Application No. PCT/EP2016/067363, dated Oct. 27, 2016, 8 pages.

Tang, et al., "A biochemical framework for RNA silencing in plants", Genes and Development, vol. 17, 2003, pp. 49-63.

Xiao, et al., "Functional analysis of the rice AP3 homologue OsMADS16 by RNA interference", Plant Molecular Biology, vol. 52, Issue 5, Jul. 2003, pp. 957-966.

Zamore, et al., "RNAi: Double-Stranded RNA Directs the ATP-Dependent Cleavage of mRNA at 21 to 23 Nucleotide Intervals", Cell, vol. 101, Issue 1, Mar. 31, 2000, pp. 25-33.

* cited by examiner

```
                        SEQUENCE LISTING

<160> NUMBER OF SEQ ID NOS: 10

<210> SEQ ID NO 1
<211> LENGTH: 1425
<212> TYPE: DNA
<213> ORGANISM: Phakopsora pachyrhizi

<400> SEQUENCE: 1
atgccggcag tgatggcagg tcccgtaacc tttgcgccac cgaaaggaaa atctagcgcg        60
atggcaattg tggttgctgg ctttgctgca tttggaggct ttttgtatgg atacgacact       120
ggatatatct ctggagtaaa agctatgcct ggttggctaa gaggagtggg ccaggttggg       180
ccagatggga attttttttct gacaactagc caagactcat tagtcaccag tattctttcc       240
ataggtactt ttgttggagc cctttttagca taccctattg gggatagata tggccgaaga       300
atcggtatag tattagcatg tttggtattt tctgctggag ttgccatgca gactatcgcc       360
gtcaagctgc cactcttcgt ggcagggaga attttttgcgg gcctgggagt tggcactgcc       420
tcttgtttgg taccaatgta tcaatcagaa tgcgcaccaa aatggattcg aggaggagtc       480
gtcgcgtgct accaatttgc catcactata ggtctcttat gtgcttctgt cgcggtgaat       540
gctaccaaag atatcgattc tacagcgtgc tatcggattc cgattggaat tcagttcatt       600
tgggctttca tcctatgtgc tggattgata attttacccg aatcgccacg atatttgctt       660
```

```
ttaaagggta gagaagatga agcattgaaa tctttgatgc gactatacag tgcaccgatg    720
gatgatccgg atgtacaggc cgaattctct gaaataaatg caaacctaga aaggagagg    780
tcttttggac gcacaacctt gttagactgt ttcaaaagcg atcatcgaaa aaatctcctc    840
aggactatga ctggtatcgg ctgtcaaggt tggcaacaag cttctggaat aaacttcttt    900
ttttactacg gcactacatt cttcaaaaat tctggaatct ctaacccatt cactgttact    960
gtggccagca acgttgtaaa tgttgtggcg accattccag gaatttgggc agttgataaa   1020
cttgggcgta gatcactctt actaatggga gcatttgcaa tgtttgcgtg tgaacttgtt   1080
gttgcttgca ttggaacgtt tactaagagc gataacatgt cgtcgcagaa agttttagtg   1140
gttttctctt gcctttccat cggagttttt gctgccacgt ggggacccat cccatgggta   1200
gtgactagtg aaatataccc tcttgcaacg cgagggaagc agatggcaat gtcaacagct   1260
tccaattggg ggataaattt ttttataggt ttcataacac cttacttggt tgacgaaggc   1320
gccggaaaag ctggtctagg cgtaaaagtt ttcttttat gggcttgtac ttcatttgga   1380
gggttcctat ttgcgttttt ctttattcct gaaacaaaag gctc                   1425
```

<210> SEQ ID NO 2
<211> LENGTH: 475
<212> TYPE: PRT
<213> ORGANISM: Phakopsora pachyrhizi

<400> SEQUENCE: 2

```
Met Pro Ala Val Met Ala Gly Pro Val Thr Phe Ala Pro Pro Lys Gly
1               5                   10                  15

Lys Ser Ser Ala Met Ala Ile Val Ala Gly Phe Ala Ala Phe Gly
            20                  25                  30

Gly Phe Leu Tyr Gly Tyr Asp Thr Gly Tyr Ile Ser Gly Val Lys Ala
        35                  40                  45

Met Pro Gly Trp Leu Arg Gly Val Gly Gln Val Gly Pro Asp Gly Asn
    50                  55                  60

Phe Phe Leu Thr Thr Ser Gln Asp Ser Leu Val Thr Ser Ile Leu Ser
65                  70                  75                  80

Ile Gly Thr Phe Val Gly Ala Leu Leu Ala Tyr Pro Ile Gly Asp Arg
                85                  90                  95

Tyr Gly Arg Arg Ile Gly Ile Val Leu Ala Cys Leu Val Phe Ser Ala
            100                 105                 110

Gly Val Ala Met Gln Thr Ile Ala Val Lys Leu Pro Leu Phe Val Ala
        115                 120                 125

Gly Arg Ile Phe Ala Gly Leu Gly Val Gly Thr Ala Ser Cys Leu Val
    130                 135                 140

Pro Met Tyr Gln Ser Glu Cys Ala Pro Lys Trp Ile Arg Gly Gly Val
145                 150                 155                 160

Val Ala Cys Tyr Gln Phe Ala Ile Thr Ile Gly Leu Leu Cys Ala Ser
                165                 170                 175

Val Ala Val Asn Ala Thr Lys Asp Ile Asp Ser Thr Ala Cys Tyr Arg
            180                 185                 190

Ile Pro Ile Gly Ile Gln Phe Ile Trp Ala Phe Ile Leu Cys Ala Gly
        195                 200                 205

Leu Ile Ile Leu Pro Glu Ser Pro Arg Tyr Leu Leu Leu Lys Gly Arg
    210                 215                 220

Glu Asp Glu Ala Leu Lys Ser Leu Met Arg Leu Tyr Ser Ala Pro Met
225                 230                 235                 240
```

```
Asp Asp Pro Asp Val Gln Ala Glu Phe Ser Glu Ile Asn Ala Asn Leu
            245                 250                 255

Glu Lys Glu Arg Ser Phe Gly Arg Thr Thr Leu Leu Asp Cys Phe Lys
        260                 265                 270

Ser Asp His Arg Lys Asn Leu Leu Arg Thr Met Thr Gly Ile Gly Cys
    275                 280                 285

Gln Gly Trp Gln Gln Ala Ser Gly Ile Asn Phe Phe Tyr Tyr Gly
290                 295                 300

Thr Thr Phe Phe Lys Asn Ser Gly Ile Ser Asn Pro Phe Thr Val Thr
305                 310                 315                 320

Val Ala Ser Asn Val Val Asn Val Val Ala Thr Ile Pro Gly Ile Trp
                325                 330                 335

Ala Val Asp Lys Leu Gly Arg Arg Ser Leu Leu Leu Met Gly Ala Phe
            340                 345                 350

Ala Met Phe Ala Cys Glu Leu Val Val Ala Cys Ile Gly Thr Phe Thr
        355                 360                 365

Lys Ser Asp Asn Met Ser Ser Gln Lys Val Leu Val Phe Ser Cys
    370                 375                 380

Leu Ser Ile Gly Val Phe Ala Ala Thr Trp Gly Pro Ile Pro Trp Val
385                 390                 395                 400

Val Thr Ser Glu Ile Tyr Pro Leu Ala Thr Arg Gly Lys Gln Met Ala
                405                 410                 415

Met Ser Thr Ala Ser Asn Trp Gly Ile Asn Phe Ile Gly Phe Ile
            420                 425                 430

Thr Pro Tyr Leu Val Asp Glu Gly Ala Gly Lys Ala Gly Leu Gly Val
        435                 440                 445

Lys Val Phe Phe Leu Trp Ala Cys Thr Ser Phe Gly Gly Phe Leu Phe
    450                 455                 460

Ala Phe Phe Phe Ile Pro Glu Thr Lys Gly Leu
465                 470                 475
```

<210> SEQ ID NO 3
<211> LENGTH: 1569
<212> TYPE: DNA
<213> ORGANISM: Uromyces fabae

<400> SEQUENCE: 3

```
atgcctgcgg ttatggccgg cccggtctct ttcgccccgc cggagggtaa atctagtaag      60
gtcgcgattg tcattgctgt atttgccgcc tttggtggct tcttatatgg atatgacact     120
ggttacattg ccggagttaa agccatgccc ttttggctac gctctgctgg acagcgcgga     180
cctgatggta atacatgat cactacaagc caagactcaa tggttactag tattctttca     240
gttgggactt tcgtgggagc tcttttagcc tatcctatcg gtgacaggtt cggacgaaga     300
attggcataa tgattgcctg tgcaattttt tctgttggtg ttgctctgca aactgcctca     360
accaagatac aatgttcgt cgtcggcaga gtttttgctg gcttaggagt tggggtagct     420
tcttgtcttg tgccaatgta tcaatcagaa tgtgcaccaa atggatacg tggagggatt     480 gtcgcgtgct accatgggc tattaccatt ggtttattag ttgcctcaat tacggtcaac     540
gcaacgaaag atttcgacag tgccaactca taccgcattc ccattggtat tcagtttatt     600
tgggctgcaa tccttactat cggtttgctt gtgttacccg aatcgccgag atacttacta     660
ctcaagggca gggaagacga ggcttggaaa tctttaagtc gcctctacag cgctccatac     720
gatgacccag atgtacaagc agaattctca gaaatcatgg ctagtttgga aaagagaga     780
```

-continued

```
tcgttcggaa aaaccacgtt actagactgc ttcaaaacag acaaagaaa aaatctccaa      840
aggactttga caggtttggg cgttcaggga tggcaacaag cgtcgggaat taattttttc     900
ttttattacg gtacaacgtt cttcaaaaat gcgggaatcg aaaacgcgtt tctagtgacg     960
gtcgcaacta atgtagtcaa tgtggttatg actataccag gaatttgggc cgtagacaaa    1020
gtaggtcgca gaacgatgat gatttgtggg gcagcgatga tgttcacatg tgaacttatc    1080
ctggcttgcg ttggtacttt cactgcaact agcaacctag cctcgcagaa agttctcgtg    1140
gccttctctt gtatcttcat cggtcttttt gcggccactt ggggcccgat tccctgggtt    1200
gtgacaagcg agatttatcc gctcgcgacc cgtggtaagc aaatggcaat gtcaaccgcc    1260
tcaaattggg cagtgaattt tttcattggt ttcattacgc catacttggt cgattcgggt    1320
gccggtcaag ccggcttggg tgttaaagtc ttctggcttt gggctgcttt gtgctttgga    1380
gccatggtgt tctcattctt acttatccct gagacgaaag gactttcgct ggagcaagtt    1440
gacctccttt acactaattc taccgtcctt aagagcaata cctacaggag ccagttgatc    1500
gcaaacaact tgcacgaggg tatgacacct gcagaaaagg cataccaaga gaaattggaa    1560
catatttga                                                            1569
```

```
<210> SEQ ID NO 4
<211> LENGTH: 522
<212> TYPE: PRT
<213> ORGANISM: Uromyces fabae

<400> SEQUENCE: 4
```

Met Pro Ala Val Met Ala Gly Pro Val Ser Phe Ala Pro Pro Glu Gly
1               5                   10                  15

Lys Ser Ser Lys Val Ala Ile Val Ile Ala Val Phe Ala Ala Phe Gly
            20                  25                  30

Gly Phe Leu Tyr Gly Tyr Asp Thr Gly Tyr Ile Ala Gly Val Lys Ala
        35                  40                  45

Met Pro Phe Trp Leu Arg Ser Ala Gly Gln Arg Gly Pro Asp Gly Lys
    50                  55                  60

Tyr Met Ile Thr Thr Ser Gln Asp Ser Met Val Thr Ser Ile Leu Ser
65                  70                  75                  80

Val Gly Thr Phe Val Gly Ala Leu Leu Ala Tyr Pro Ile Gly Asp Arg
                85                  90                  95

Phe Gly Arg Arg Ile Gly Ile Met Ile Ala Cys Ala Ile Phe Ser Val
            100                 105                 110

Gly Val Ala Leu Gln Thr Ala Ser Thr Lys Ile Pro Met Phe Val Val
        115                 120                 125

Gly Arg Val Phe Ala Gly Leu Gly Val Gly Val Ala Ser Cys Leu Val
    130                 135                 140

Pro Met Tyr Gln Ser Glu Cys Ala Pro Lys Trp Ile Arg Gly Gly Ile
145                 150                 155                 160

Val Ala Cys Tyr Gln Trp Ala Ile Thr Ile Gly Leu Leu Val Ala Ser
                165                 170                 175

Ile Thr Val Asn Ala Thr Lys Asp Phe Asp Ser Ala Asn Ser Tyr Arg
            180                 185                 190

Ile Pro Ile Gly Ile Gln Phe Ile Trp Ala Ala Ile Leu Thr Ile Gly
        195                 200                 205

Leu Leu Val Leu Pro Glu Ser Pro Arg Tyr Leu Leu Lys Gly Arg
    210                 215                 220

Glu Asp Glu Ala Trp Lys Ser Leu Ser Arg Leu Tyr Ser Ala Pro Tyr

```
                    225                 230                 235                 240
        Asp Asp Pro Asp Val Gln Ala Glu Phe Ser Glu Ile Met Ala Ser Leu
                        245                 250                 255

Glu Lys Glu Arg Ser Phe Gly Lys Thr Thr Leu Leu Asp Cys Phe Lys
                        260                 265                 270

Thr Asp Lys Arg Lys Asn Leu Gln Arg Thr Leu Thr Gly Leu Gly Val
                        275                 280                 285

Gln Gly Trp Gln Gln Ala Ser Gly Ile Asn Phe Phe Tyr Tyr Gly
            290                 295                 300

Thr Thr Phe Phe Lys Asn Ala Gly Ile Glu Asn Ala Phe Leu Val Thr
        305                 310                 315                 320

Val Ala Thr Asn Val Val Asn Val Val Met Thr Ile Pro Gly Ile Trp
                        325                 330                 335

Ala Val Asp Lys Val Gly Arg Arg Thr Met Met Ile Cys Gly Ala Ala
                        340                 345                 350

Met Met Phe Thr Cys Glu Leu Ile Leu Ala Cys Val Gly Thr Phe Thr
                        355                 360                 365

Ala Thr Ser Asn Leu Ala Ser Gln Lys Val Leu Val Ala Phe Ser Cys
                        370                 375                 380

Ile Phe Ile Gly Leu Phe Ala Ala Thr Trp Gly Pro Ile Pro Trp Val
        385                 390                 395                 400

Val Thr Ser Glu Ile Tyr Pro Leu Ala Thr Arg Gly Lys Gln Met Ala
                        405                 410                 415

Met Ser Thr Ala Ser Asn Trp Ala Val Asn Phe Phe Ile Gly Phe Ile
                        420                 425                 430

Thr Pro Tyr Leu Val Asp Ser Gly Ala Gly Gln Ala Gly Leu Gly Val
                        435                 440                 445

Lys Val Phe Trp Leu Trp Ala Ala Leu Cys Phe Gly Ala Met Val Phe
                        450                 455                 460

Ser Phe Leu Leu Ile Pro Glu Thr Lys Gly Leu Ser Leu Glu Gln Val
        465                 470                 475                 480

Asp Leu Leu Tyr Thr Asn Ser Thr Val Leu Lys Ser Asn Thr Tyr Arg
                        485                 490                 495

Ser Gln Leu Ile Ala Asn Asn Leu His Glu Gly Met Thr Pro Ala Glu
                        500                 505                 510

Lys Ala Tyr Gln Glu Lys Leu Glu His Ile
                        515                 520

<210> SEQ ID NO 5
<211> LENGTH: 1566
<212> TYPE: DNA
<213> ORGANISM: Puccinia striiformis

<400> SEQUENCE: 5
atgcctgccg tagccggtcc ggtctctttc gccccgccgg agggcaaatc tagtaaaatg      60
gcgatcatca ttgccgggtt tgctgccttt ggtggctttc tttacggata cgatactggc     120
tacattgcgg gagtgaaagc tatgccattc tggttgcgct ctgctggaca gctcggatca     180
gacggtaaat attcgattac taccagtcaa gactctctcg ttactagtat tctttcagtc     240
ggaacttttg tcggtgccct tttagcttat cccatcggag acaggtatgg aaggaggata     300
ggtataatga tcgcgtgcgc gatattctcc gttggggttg ccttgcaaac tgcatcatcc     360
accataccat tatttgtcgt cgggagagta ttcgccgggc tggagtcgg tgttgcatct     420 tgccttgtgc cgatgtatca atcggaatgt gcaccaaaat ggatccgcgg gggtgtcgtt     480
```

-continued

```
gcatgctatc aatgggccat caccattgga ttgctagtcg catcagtaac tgtgaacgcg      540
acgaaagatt tcgacagtgc aaacagttac cgcattccaa ttggaatcca gttcgtttgg      600
gcagcgatcc tcgtcattgg cttaaccgtt ctgccagagt cacctcgata tttactcttg      660
aaggggaatg aagaagaggc ctggaaatcc ctgagtcggc tgtatagtgc tccatatgat      720
gacccggacg tccaggcgga attctcagaa atcatggcca gcttggaaaa agagagatct      780
ttcggaaaga cgagcttgct cgattgtttc aaaactgaca agagaaaaaa tctccaaagg      840
acccttacag gattgggagt tcaaggatgg caacaagcgt cgggtatcaa cttcttcttt      900
tactacggca acattcttt aaaaattcc ggaatcgaaa acgccttcct ggtcacagta      960
gcaaccaatg tagttaacgt ggtggcgacc attccaggaa tttgggccgt agacaaagtt     1020
ggacgtagaa caatgttgat tgccggagcg atgatgatgt tggttgcga gctcattgtc     1080 gcttgtgtcg aacatttac tacggccgac aaccaagctt cccagaaagt tcttgtagct     1140
ttctcttgta tcttcatcgg ggttttgcc gccacctggg gtccaatccc ttgggtcgtt     1200
acaagtgaaa tctaccctct tgctactcgt ggaaaacaga tggccatgtc taccgcctcc     1260
aactgggtag ttaactttt catcggttc atcaccccctt acctagttga cggggggtgct     1320 ggtaaagctg gcctgggtgt caaagtattc tggctctggg ccgcgttgtg ctttgcagct     1380
ttgacgtttt cgttcttctt gatccccgag accaagggac tttcactgga gcaggttgat     1440 ctccttttaca ccaactcgac tgttctcaag agcaactctt acagacttca attgatcgcc     1500
aacaacttgc acgagggtat gacccccgcc gagaaggctt accaagagaa gctggagcac     1560
atttga                                                                1566
```

<210> SEQ ID NO 6
<211> LENGTH: 521
<212> TYPE: PRT
<213> ORGANISM: Puccinia striiformis

<400> SEQUENCE: 6

```
Met Pro Ala Val Ala Gly Pro Val Ser Phe Ala Pro Glu Gly Lys
1               5                   10                  15

Ser Ser Lys Met Ala Ile Ile Ile Ala Gly Phe Ala Ala Phe Gly Gly
                20                  25                  30

Phe Leu Tyr Gly Tyr Asp Thr Gly Tyr Ile Ala Gly Val Lys Ala Met
            35                  40                  45

Pro Phe Trp Leu Arg Ser Ala Gly Gln Leu Gly Ser Asp Gly Lys Tyr
        50                  55                  60

Ser Ile Thr Thr Ser Gln Asp Ser Leu Val Thr Ser Ile Leu Ser Val
65                  70                  75                  80

Gly Thr Phe Val Gly Ala Leu Leu Ala Tyr Pro Ile Gly Asp Arg Tyr
                85                  90                  95

Gly Arg Arg Ile Gly Ile Met Ile Ala Cys Ala Ile Phe Ser Val Gly
                100                 105                 110

Val Ala Leu Gln Thr Ala Ser Ser Thr Ile Pro Leu Phe Val Val Gly
            115                 120                 125

Arg Val Phe Ala Gly Leu Gly Val Gly Val Ala Ser Cys Leu Val Pro
        130                 135                 140

Met Tyr Gln Ser Glu Cys Ala Pro Lys Trp Ile Arg Gly Gly Val Val
145                 150                 155                 160

Ala Cys Tyr Gln Trp Ala Ile Thr Ile Gly Leu Leu Val Ala Ser Val
                165                 170                 175
```

```
Thr Val Asn Ala Thr Lys Asp Phe Asp Ser Ala Asn Ser Tyr Arg Ile
            180                 185                 190

Pro Ile Gly Ile Gln Phe Val Trp Ala Ala Ile Leu Val Ile Gly Leu
            195                 200                 205

Thr Val Leu Pro Glu Ser Pro Arg Tyr Leu Leu Lys Gly Asn Glu
            210                 215                 220

Glu Glu Ala Trp Lys Ser Leu Ser Arg Leu Tyr Ser Ala Pro Tyr Asp
225                 230                 235                 240

Asp Pro Asp Val Gln Ala Glu Phe Ser Glu Ile Met Ala Ser Leu Glu
                245                 250                 255

Lys Glu Arg Ser Phe Gly Lys Thr Ser Leu Leu Asp Cys Phe Lys Thr
            260                 265                 270

Asp Lys Arg Lys Asn Leu Gln Arg Thr Leu Thr Gly Leu Gly Val Gln
            275                 280                 285

Gly Trp Gln Gln Ala Ser Gly Ile Asn Phe Phe Tyr Tyr Gly Thr
            290                 295                 300

Thr Phe Phe Lys Asn Ser Gly Ile Glu Asn Ala Phe Leu Val Thr Val
305                 310                 315                 320

Ala Thr Asn Val Val Asn Val Val Ala Thr Ile Pro Gly Ile Trp Ala
                325                 330                 335

Val Asp Lys Val Gly Arg Arg Thr Met Leu Ile Ala Gly Ala Met Met
            340                 345                 350

Met Phe Gly Cys Glu Leu Ile Val Ala Cys Val Gly Thr Phe Thr Thr
            355                 360                 365

Ala Asp Asn Gln Ala Ser Gln Lys Val Leu Val Ala Phe Ser Cys Ile
            370                 375                 380

Phe Ile Gly Val Phe Ala Ala Thr Trp Gly Pro Ile Pro Trp Val Val
385                 390                 395                 400

Thr Ser Glu Ile Tyr Pro Leu Ala Thr Arg Gly Lys Gln Met Ala Met
                405                 410                 415

Ser Thr Ala Ser Asn Trp Val Val Asn Phe Phe Ile Gly Phe Ile Thr
            420                 425                 430

Pro Tyr Leu Val Asp Gly Gly Ala Gly Lys Ala Gly Leu Gly Val Lys
            435                 440                 445

Val Phe Trp Leu Trp Ala Ala Leu Cys Phe Ala Ala Leu Thr Phe Ser
450                 455                 460

Phe Phe Leu Ile Pro Glu Thr Lys Gly Leu Ser Leu Glu Gln Val Asp
465                 470                 475                 480

Leu Leu Tyr Thr Asn Ser Thr Val Leu Lys Ser Asn Ser Tyr Arg Leu
                485                 490                 495

Gln Leu Ile Ala Asn Asn Leu His Glu Gly Met Thr Pro Ala Glu Lys
            500                 505                 510

Ala Tyr Gln Glu Lys Leu Glu His Ile
            515                 520

<210> SEQ ID NO 7
<211> LENGTH: 1656
<212> TYPE: DNA
<213> ORGANISM: Puccinia graminis

<400> SEQUENCE: 7
atgcctgcgg taatggccgg tccggtcact tttgccccgc cggagggcaa atctagcaag    60
atggctatca tcattgccgg attcgctgcc tttggtggtt tcctgtatgg atacgacact   120
```

```
ggctacatcg cgggagtcaa agcgatgcca ttctggttac gttctgctgg acagcttgga      180
ccagatggta aatatatgat taccaccggc caagattctc ttgttaccag tatcctctca      240
gtcgggactt tgtcggcgc acttttagct tatcccattg agacaggtt tggtcggcga       300
ataggcataa tgatcgcgtg tgcgattttc tccgtgggcg ttgccttgca aactgcttca      360
accaccatac cgttatttgt cgtcgggagg gtattcgccg gcctgggagt tggtgttgca      420
tcttgccttg tgccaatgta tcaatcggaa tgtgcaccaa aatggattcg cggaggtgtg      480
gttgcatgct atcaatgggc catcaccatc ggattactag tggcttcggt aacggtgaac      540
gcgacaaaag atttcaacag tgccaacagc tatcgcattc ccattggcat tcagtttgtt      600
tgggcagcaa tccttgtgat cggtttggcc atattgccgg aatctccgcg atacttactc      660
ctcaagggaa gagaagatga agcctggaag tctcttagcc ggctgtacag tgctccgtat      720
gatgacccgg atgtacaagc ggaattctca gaaattatgg ctaatctgga aaggagagg       780
tctttcggaa agactacttt gctcgactgc ttcaaaacag acaagagaaa aaatcttcaa      840
aggaccttga ctgggctggg agttcaggga tggcaacaag cggtattcgg gtatcaattt      900
gtacgtgaaa tacgcgaatt cgctgcctct cagagaaaag aaaaactgac agaaattttc      960
acctatcgtt actcaaccat cagcttcttc tattatggca ctacctttt caaaaattct    1020
ggaatcgaga acgccttcct ggtaacggta ttgaccaatg tagtcaacgt agtagcaacc    1080
atcccaggaa tttgggcggt agacaaagtt ggtcgcagga cgatgttgat tgctggagcg    1140
gcaatgatgt ttacttgcga actcatcgtt gcatgtgttg gaacttttac tacggctgac    1200
aaccaagcat cacagaaagt tcttgtggct ttctcttgca tcttcatcgg aattttcgcc    1260
gctacctggg gtcccgtacc ttgggttgtc acgagcgaaa tttacccact tgccactcgt    1320
ggcaaacaga tggcaatgtc caccgcttcc aactgggtag ttaactttt catcgggttc    1380
atcaccccctt acttggttga tgctggtccc ggtcaggctg gcctgggtgt caaagtcttt    1440
tggctttggg ccgctttgtg ttttgcagct ttgacgtttt cattcttctt gatccccgag    1500
actaagggcc tttcactgga gcaagttgat ctcctataca ccaactcaac tgttctcaag    1560
agtaattcgt acagaaccca attgatcgcg aacaacctgc acgagggaat gacgcctgcc    1620
gagaaggcct accaagagaa actggagcat atttga                              1656
```

<210> SEQ ID NO 8
<211> LENGTH: 551
<212> TYPE: PRT
<213> ORGANISM: Puccinia graminis
<400> SEQUENCE: 8

```
Met Pro Ala Val Met Ala Gly Pro Val Thr Phe Ala Pro Pro Glu Gly
1               5                  10                  15

Lys Ser Ser Lys Met Ala Ile Ile Ile Ala Gly Phe Ala Ala Phe Gly
            20                  25                  30

Gly Phe Leu Tyr Gly Tyr Asp Thr Gly Tyr Ile Ala Gly Val Lys Ala
        35                  40                  45

Met Pro Phe Trp Leu Arg Ser Ala Gly Gln Leu Gly Pro Asp Gly Lys
    50                  55                  60

Tyr Met Ile Thr Thr Gly Gln Asp Ser Leu Val Thr Ser Ile Leu Ser
65                  70                  75                  80

Val Gly Thr Phe Val Gly Ala Leu Leu Ala Tyr Pro Ile Gly Asp Arg
                85                  90                  95

Phe Gly Arg Arg Ile Gly Ile Met Ile Ala Cys Ala Ile Phe Ser Val
```

```
            100                 105                 110
Gly Val Ala Leu Gln Thr Ala Ser Thr Thr Ile Pro Leu Phe Val Val
            115                 120                 125
Gly Arg Val Phe Ala Gly Leu Gly Val Gly Val Ala Ser Cys Leu Val
            130                 135                 140
Pro Met Tyr Gln Ser Glu Cys Ala Pro Lys Trp Ile Arg Gly Gly Val
145                 150                 155                 160
Val Ala Cys Tyr Gln Trp Ala Ile Thr Ile Gly Leu Leu Val Ala Ser
                    165                 170                 175
Val Thr Val Asn Ala Thr Lys Asp Phe Asn Ser Ala Asn Ser Tyr Arg
                    180                 185                 190
Ile Pro Ile Gly Ile Gln Phe Val Trp Ala Ala Ile Leu Val Ile Gly
                    195                 200                 205
Leu Ala Ile Leu Pro Glu Ser Pro Arg Tyr Leu Leu Leu Lys Gly Arg
            210                 215                 220
Glu Asp Glu Ala Trp Lys Ser Leu Ser Arg Leu Tyr Ser Ala Pro Tyr
225                 230                 235                 240
Asp Asp Pro Asp Val Gln Ala Glu Phe Ser Glu Ile Met Ala Asn Leu
                    245                 250                 255
Glu Lys Glu Arg Ser Phe Gly Lys Thr Thr Leu Leu Asp Cys Phe Lys
                    260                 265                 270
Thr Asp Lys Arg Lys Asn Leu Gln Arg Thr Leu Thr Gly Leu Gly Val
                    275                 280                 285
Gln Gly Trp Gln Gln Ala Val Phe Gly Tyr Gln Phe Val Arg Glu Ile
            290                 295                 300
Arg Glu Phe Ala Ala Ser Gln Arg Lys Glu Lys Leu Thr Glu Ile Phe
305                 310                 315                 320
Thr Tyr Arg Tyr Ser Thr Ile Ser Phe Phe Tyr Tyr Gly Thr Thr Phe
                    325                 330                 335
Phe Lys Asn Ser Gly Ile Glu Asn Ala Phe Leu Val Thr Val Leu Thr
                    340                 345                 350
Asn Val Val Asn Val Val Ala Thr Ile Pro Gly Ile Trp Ala Val Asp
                    355                 360                 365
Lys Val Gly Arg Arg Thr Met Leu Ile Ala Gly Ala Ala Met Met Phe
            370                 375                 380
Thr Cys Glu Leu Ile Val Ala Cys Val Gly Thr Phe Thr Thr Ala Asp
385                 390                 395                 400
Asn Gln Ala Ser Gln Lys Val Leu Val Ala Phe Ser Cys Ile Phe Ile
                    405                 410                 415
Gly Ile Phe Ala Ala Thr Trp Gly Pro Val Pro Trp Val Val Thr Ser
                    420                 425                 430
Glu Ile Tyr Pro Leu Ala Thr Arg Gly Lys Gln Met Ala Met Ser Thr
                    435                 440                 445
Ala Ser Asn Trp Val Val Asn Phe Phe Ile Gly Phe Ile Thr Pro Tyr
            450                 455                 460
Leu Val Asp Ala Gly Pro Gly Gln Ala Gly Leu Gly Val Lys Val Phe
465                 470                 475                 480
Trp Leu Trp Ala Ala Leu Cys Phe Ala Ala Leu Thr Phe Ser Phe Phe
                    485                 490                 495
Leu Ile Pro Glu Thr Lys Gly Leu Ser Leu Glu Gln Val Asp Leu Leu
                    500                 505                 510
Tyr Thr Asn Ser Thr Val Leu Lys Ser Asn Ser Tyr Arg Thr Gln Leu
                    515                 520                 525
```

Ile Ala Asn Asn Leu His Glu Gly Met Thr Pro Ala Glu Lys Ala Tyr
          530                 535                 540

Gln Glu Lys Leu Glu His Ile
545                 550

<210> SEQ ID NO 9
<211> LENGTH: 1569
<212> TYPE: DNA
<213> ORGANISM: Puccunia triticina

<400> SEQUENCE: 9

| | |
|---|---:|
| atgcctgcag taatggccgg tccggtcact ttcgccccgc cggagggcaa atccagcaaa | 60 |
| atggctatca tcatagccgg attcgccgct tttggcggct ttctctatgg gtacgatacg | 120 |
| ggctacatcg ccggagttaa agcaatgcca ttctggttac gctctgctgg acagcttgga | 180 |
| ccagatggta atacatgat taccaccggc aagattccc tggttaccag tatcctatca | 240 |
| gttggaactt tcgttggtgc actgttggct tatcccatcg agataggta tggacgaaaa | 300 |
| ataggtatca tgatcgcatg cgcgattttc tctatcggtg tcgccttgca aactgcatca | 360 |
| accaccatac cgttattcgt cgttgggagg gtattcgccg tctgggagt tggtgttgca | 420 |
| tcttgtctgg tgccaatgta tcaatcggaa tgtgcaccaa aatggattcg cggggggtgtt | 480 |
| gttgcatgtt atcaatgggc gatcactatc ggcttactag tggcttcagt aacggtcaac | 540 |
| gcgacgaaag acttcgatag tgccaactcc taccgcattc ctattggtat ccagtttgtt | 600 |
| tgggcagcaa tcctcgtgat tggtttggcc atattgccag aatctccacg atatttactt | 660 |
| ctcaagggga gagaagatga agcctggaag tccctgagtc gactgtatag tgctccctat | 720 |
| gatgacccag atgtgcaagc ggaattctca gaaattatgg ccagcttgga aaaagagcga | 780 |
| tctttcggaa agacgacctt gctcgactgt ttcaaaacag ataagagaaa aaacctgcaa | 840 |
| aggacgttga ctggactggg ggttcaaggc tggcaacaag cgtcgggtat caactttttt | 900 |
| ttttattatg gtactacctt cttcaagaat tcagggatca aagacgcctt cctggtgaca | 960 |
| gtcgcaacca acgtagtgaa cgttgtggcc accatcccag gaatttgggc agtggacaaa | 1020 |
| gttggtcgta gaacaatgtt gatcgctgga gcggcgatga tgtttgcttg cgaattcatt | 1080 |
| gttgcttgtg tcggaacgtt tacctcggct aacaacatgg cctcccagaa agttcttgta | 1140 |
| gctttctctt gcatcttcat cggaattttt gccgcaacct ggggtcccgt ccctggggtc | 1200 |
| gttacgagtg aaatctaccc acttgctact cgtggcaaac agatggcgat gtcaaccgcc | 1260 |
| tccaactggg cagttaactt tttcatcggg ttcatcactc cttacttagt tgacacagga | 1320 |
| gctggtcagg ctggcctcgg cgtcaaagtt ttttggcttt gggccgcttt gtgttttgca | 1380 |
| gctctgctgt tttcattctt ctttatcccc gagaccaagg gtctctcact cgagcaagtt | 1440 |
| gatctcctgt acaccaactc gactgttctc aagagtaact cttacaggct tcagttgatc | 1500 |
| gcaaacaacc tccacgaggg tatgacgcct gcagaaaagg cctaccaaga gaagctggag | 1560 |
| catatttga | 1569 |

<210> SEQ ID NO 10
<211> LENGTH: 522
<212> TYPE: PRT
<213> ORGANISM: Puccunia triticina

<400> SEQUENCE: 10

Met Pro Ala Val Met Ala Gly Pro Val Thr Phe Ala Pro Pro Glu Gly
1               5                   10                  15

```
Lys Ser Ser Lys Met Ala Ile Ile Ala Gly Phe Ala Ala Phe Gly
             20                  25                  30

Gly Phe Leu Tyr Gly Tyr Asp Thr Gly Tyr Ile Ala Gly Val Lys Ala
             35                  40                  45

Met Pro Phe Trp Leu Arg Ser Ala Gly Gln Leu Gly Pro Asp Gly Lys
 50                  55                  60

Tyr Met Ile Thr Thr Gly Gln Asp Ser Leu Val Thr Ser Ile Leu Ser
 65                  70                  75                  80

Val Gly Thr Phe Val Gly Ala Leu Leu Ala Tyr Pro Ile Gly Asp Arg
                 85                  90                  95

Tyr Gly Arg Lys Ile Gly Ile Met Ile Ala Cys Ala Ile Phe Ser Ile
                100                 105                 110

Gly Val Ala Leu Gln Thr Ala Ser Thr Thr Ile Pro Leu Phe Val Val
            115                 120                 125

Gly Arg Val Phe Ala Gly Leu Gly Val Gly Val Ala Ser Cys Leu Val
    130                 135                 140

Pro Met Tyr Gln Ser Glu Cys Ala Pro Lys Trp Ile Arg Gly Gly Val
145                 150                 155                 160

Val Ala Cys Tyr Gln Trp Ala Ile Thr Ile Gly Leu Leu Val Ala Ser
                165                 170                 175

Val Thr Val Asn Ala Thr Lys Asp Phe Asp Ser Ala Asn Ser Tyr Arg
            180                 185                 190

Ile Pro Ile Gly Ile Gln Phe Val Trp Ala Ala Ile Leu Val Ile Gly
        195                 200                 205

Leu Ala Ile Leu Pro Glu Ser Pro Arg Tyr Leu Leu Leu Lys Gly Arg
    210                 215                 220

Glu Asp Glu Ala Trp Lys Ser Leu Ser Arg Leu Tyr Ser Ala Pro Tyr
225                 230                 235                 240

Asp Asp Pro Asp Val Gln Ala Glu Phe Ser Glu Ile Met Ala Ser Leu
                245                 250                 255

Glu Lys Glu Arg Ser Phe Gly Lys Thr Thr Leu Leu Asp Cys Phe Lys
            260                 265                 270

Thr Asp Lys Arg Lys Asn Leu Gln Arg Thr Leu Thr Gly Leu Gly Val
        275                 280                 285

Gln Gly Trp Gln Gln Ala Ser Gly Ile Asn Phe Phe Tyr Tyr Gly
    290                 295                 300

Thr Thr Phe Phe Lys Asn Ser Gly Ile Lys Asp Ala Phe Leu Val Thr
305                 310                 315                 320

Val Ala Thr Asn Val Val Asn Val Val Ala Thr Ile Pro Gly Ile Trp
                325                 330                 335

Ala Val Asp Lys Val Gly Arg Arg Thr Met Leu Ile Ala Gly Ala Ala
            340                 345                 350

Met Met Phe Ala Cys Glu Phe Ile Val Ala Cys Val Gly Thr Phe Thr
        355                 360                 365

Ser Ala Asn Asn Met Ala Ser Gln Lys Val Leu Val Ala Phe Ser Cys
    370                 375                 380

Ile Phe Ile Gly Ile Phe Ala Ala Thr Trp Gly Pro Val Pro Trp Val
385                 390                 395                 400

Val Thr Ser Glu Ile Tyr Pro Leu Ala Thr Arg Gly Lys Gln Met Ala
                405                 410                 415

Met Ser Thr Ala Ser Asn Trp Ala Val Asn Phe Phe Ile Gly Phe Ile
            420                 425                 430
```

```
Thr Pro Tyr Leu Val Asp Thr Gly Ala Gly Gln Ala Gly Leu Gly Val
        435                 440                 445

Lys Val Phe Trp Leu Trp Ala Ala Leu Cys Phe Ala Ala Leu Leu Phe
    450                 455                 460

Ser Phe Phe Phe Ile Pro Glu Thr Lys Gly Leu Ser Leu Glu Gln Val
465                 470                 475                 480

Asp Leu Leu Tyr Thr Asn Ser Thr Val Leu Lys Ser Asn Ser Tyr Arg
                485                 490                 495

Leu Gln Leu Ile Ala Asn Asn Leu His Glu Gly Met Thr Pro Ala Glu
                500                 505                 510

Lys Ala Tyr Gln Glu Lys Leu Glu His Ile
        515                 520
```

METHODS AND COMPOSITIONS FOR THE CONTROL OF RUST FUNGI BY INHIBITING EXPRESSION OF THE HXT1 GENE

CROSS REFERENCE TO RELATED APPLICATIONS

This application is a 35 U.S.C. 371 National Phase of PCT Application No. PCT/EP2016/067363 filed Jul. 21, 2016, which claims benefit to EP Application No. 15290196.3 filed Jul. 30, 2015, the disclosure of which is hereby incorporated by reference in its entirety.

The present invention relates to methods for the control of plant fungal pathogens, particularly rusts, by inhibiting one or more biological functions of such plant fungal pathogens, particularly by inhibiting the fungal HXT1 gene using RNA interference (RNAi).

The invention provides methods and compositions using RNAi against fungal genes, particularly rust fungal genes, for such control. The invention is also directed to methods for making transgenic plants tolerant to fungal pathogens, particularly rusts, and to transgenic plants and seeds generated thereof.

BACKGROUND

Plant pathogens, including fungi, bacteria, viruses, are responsible for many diseases on cultivated crops, which can lead to significant crop losses usually considered to be between 20 to 40% of expected yields.

Rusts are plant diseases caused by fungal basidiomycete pathogens of the order Pucciniales. They are considered one of the most harmful plant pathogens in agriculture. They constitute a group of devastating plant pathogens causing enormous losses on cereal and legume crops worldwide (Brown and Hovmøller, 2002, Science 297: 537-541). Their importance was highlighted in 2012, when *Puccinia* spp. infecting cereals were nominated third among the top ten fungal pathogens (Dean et al., 2012, Mol. Plant Path. 13: 414-430). Examples of economically important rust diseases include those caused by fungi of the species *Puccinia graminis, Puccinia striiformis* or *Puccinia triticina* on wheat, *Uromyces phaseoli* and *Uromyces appendiculatus* on bean, or *Phakopsora pachyrhizi* on soybean.

Asian Soybean Rust is the disease caused to soybean crops by the fungus *Phakopsora pachyrhizi*. This disease has dramatically expanded over the last years in many geographies where soybean crops are cultivated, and is causing severe losses on these crops (Hartman et al., 2011, Food Security 3: 5-17).

As of today, the most efficient means to control fungal plant pathogens, and Asian Soybean Rust in particular, are chemical fungicides. It is however of interest to explore alternative solutions against plant pathogens.

In addition to inhibiting the biological activity of certain important fungal enzymes, which is the mode of action of most fungicides, inhibiting the expression of genes that are essential for fungal growth and/or pathogenicity may be an alternative method of interest. One way to address this approach first requires the identification of the appropriate gene to inhibit, and then uses the biological mechanism known as RNA Interference or RNAi. RNAi is a natural mechanism existing in most eukaryotic organisms, including plants, to defend against certain types of microorganisms, particularly viruses, which are bearing or generating so-called "double-stranded RNAs" or "dsRNAs". Not only does it degrade dsRNAs, but if a dsRNA is identical in nucleic acid sequence to an RNA expressed by such invading microorganism, such as e.g. a messenger RNA (mRNA) coding for a certain protein, expression of this dsRNA will trigger the RNAi cellular machinery, which then leads to inhibition of translation of the mRNA into a protein.

Accordingly, the expression in the cells of an organism of a sequence homologous in nucleic acid sequence to a target gene of such organism and capable of generating double-stranded RNA molecules (dsRNA) makes it possible, very specifically, to inhibit the expression of this gene (Xiao et al., 2003, Plant Mol Biol., 52: 957-66).

A dsRNA triggers the specific degradation of a homologous RNA only in the region of sequence identity with the dsRNA (Zamore et al., 2000, Cell. 101: 25-33; Tang et al., 2003, Genes Dev. 17: 49-63). The dsRNA is an RNA molecule containing a double-stranded RNA molecule, usually of several hundreds of base pairs (bp), and including a sense strand and a complementary antisense strand. Once in a cell, the dsRNA is degraded into RNA fragments of generally 18 to 25 nucleotides called Small-Interfering RNAs (siRNA). For the RNAi mechanism to work, the resulting siRNAs shall exhibit a very high degree of sequence identity with respect to the target RNA to inhibit; however, mismatches of 3 to 4 nucleotides between the siRNA and the corresponding portion of the target RNA still make it possible for the system to operate (Tang et al., 2003, Genes Dev. 17: 49-63).

RNAi has proved to be effective when a dsRNA is injected into the nematode *Caenorhabditis elegans* (Fire et al., 1998, Nature 391: 806-811; Montgomery et al., 1998, PNAS 95: 15502-15507; WO 99/32619). Inhibition of the expression of an insect target gene has also been mentioned when the insect is fed with bacteria expressing small dsRNAs corresponding to such insect target gene (WO 01/37654).

The introduction of dsRNA was carried out in plants for different purposes, like for inducing silencing of an endogenous target gene (Hamilton et al., 1998, Plant J. 15: 737-746, WO 99/15682), for inducing resistance to RNA viruses by means of the use of a transgene expressing a dsRNA having substantial identity with respect to the viral genes (Waterhouse et al., 1998, Proc. Natl. Acad. Sci. USA 95: 13959-13964; Pandolfini et al., 2003, Biotechnol., 25; 3(1): 7, WO 98/36083, WO 99/15682, U.S. Pat. No. 5,175,102), but also for inducing resistance to nematodes (Chuang and Meyerowitz, 2000, Proc. Natl. Acad. Sci. USA 97: 4985-4990, WO 01/96584) or alternatively to the bacterium *Agrobacterium* sp. (WO 00/26346, Escobar et al., 2001, Proc. Natl. Acad. Sci. USA 98(23): 13437-13442). More recently, it has been shown that plants expressing dsRNA having substantial sequence identity against a fungal gene essential to the growth of the fungus or to its pathogenicity may also induce resistance of the plant to this fungus (WO 2005/071091).

Nevertheless, since that time, only few preliminary results and no commercial examples exist on RNAi-mediated resistance or tolerance to phytopathogenic fungi where double-stranded (dsRNA) or small interfering (siRNA) molecules are expressed in the plant, or applied as part of an external composition to the seed, the plant or to the fruit of the plant or the soil or to inert substrate wherein the plant is growing or wherein it is desired to grow.

Amongst others, one difficulty is to find an appropriate target gene, whose inhibition by dsRNA or siRNA induces an effective level of disease control, up to a level suitable for a commercial use, without deleterious effect on the plant expressing said dsRNA or siRNA or on which a composition comprising said dsRNA or siRNA is applied.

DESCRIPTION OF THE INVENTION

The present inventors have surprisingly demonstrated that inhibition of expression of the fungal HXT1 gene by means of the RNAi mechanism, in particular the use of dsRNA, results in a decrease of infection, growth, development, reproduction and/or pathogenicity of the pathogenic fungus, which may eventually result in a complete control of the disease on the infected plants.

The HXT1 gene belongs to the protein family of hexose transporters. Hexose transporters are important proteins expressed in the haustoria of biotrophic plant pathogenic fungi. Voegele et al. (2001, PNAS 98: 8133-8138) have shown that the HXT1 protein is preferably expressed in haustoria of the rust fungus *Uromyces fabae*, and that it is actually one of the most abundant proteins expressed in this fungal structure dedicated to nutrient uptake from the infected plant. These authors suggested that the HXT1 gene, almost exclusively present in fungal haustoria, makes this hexose transporter a key for the development of the rust fungus *Uromyces fabae* on its host plants.

Ten years later, Yin et al. (2011, MPMI 24: 554-561) tested the disease control potential of the RNAi mechanism using dsRNA targeting certain genes of the rust fungi *Puccinia striiformis* and *Puccinia graminis*. The dsRNA was brought into contact with the fungal cells using a viral transient dsRNA delivery system known as VIGS (Virus-Induced Gene Silencing). One of the genes tested (PSTha12O3) was reported to be homologous to the HXT1 gene identified by Voegele et al. (2001, PNAS 98: 8133-8138) in *Uromyces fabae*. Yin et al. (2011, MPMI 24: 554-561) have reported that the different genes tested show variable levels of silencing, as measured by the level of expression of the RNA transcripts of these genes. However, some of the genes tested shown good silencing levels, especially genes that are naturally abundantly expressed in fungal haustoria, and the gene PSTha12O3 was the one showing the most significant reduction in gene expression level. However, when looking at the development of the *Puccinia* rust disease on wheat plants, these authors have not observed any reduction in the development of the disease for all the genes tested, even for the HXT1-homologous gene that was observed to be the most silenced in terms of transcript abundance.

These previous findings illustrate that, although certain genes are identified as being potentially essential for growth and/or pathogenicity of the fungus, the effective silencing of those genes and the subsequent reduction of disease development is never a given. Yin et al. (2011, MPMI 24: 554-561) suggested that more factors than just the appropriate target gene may be involved in effective disease control using RNAi.

The inventors of the present invention have further explored the reasons why RNAi against the HXT1 gene, as experienced by Yin et al. (2011, MPMI 24: 554-561), although effectively silenced when dsRNA designed against this fungal target gene is used, does not lead to effective reduction in the development of the associated rust disease.

And, against the findings of Yin et al. (2011, MPMI 24: 554-561), teaching that inhibition of the HXT1 gene expression does not result in disease control or reduction, the inventors have surprisingly identified that the two *Puccinia* species used to design the dsRNA in Yin et al. (2011, MPMI 24: 554-561) each bear two sequences in their genome having homology to HXT1, and that the one that these authors have chosen to perform their RNAi experiments was not the one corresponding to the sequence coding for the HXT1 protein identified in Voegele et al. (2001, PNAS 98: 8133-8138). This finding of course questions whether the sequence indicated as "HXT1-homologue" in Yin et al. (2011, MPMI 24: 554-561) codes for an effective hexose transporter, or at least for an effective HXT1-like protein.

The inventors of the present invention have furthermore demonstrated, when using an HXT1 sequence from another fungal rust species, *Phakopsora pachyrhizi*, corresponding to the HXT1 sequence identified by Voegele et al. (2001, PNAS 98: 8133-8138) in *Uromyces fabae* and to the ones also identified in the two *Puccinia* species (but not the ones used by Yin et al., 2011, MPMI 24: 554-561), that the use of a VIGS construct expressing a dsRNA against such sequences in soybean plants (the host plant of *Phakopsora pachyrhizi*) leads not only to a decreased expression of the corresponding mRNA transcript but also to an effective reduction of the disease on plants.

The present invention therefore provides a dsRNA molecule comprising i) a first RNA strand comprising a first portion having a nucleotide sequence substantially identical to at least 18 contiguous nucleotides of the nucleotide sequence of the mRNA transcribed by a fungal HXT1 gene and ii) a second RNA strand comprising a second portion having a nucleotide sequence substantially complementary to the one of the first portion of the first strand. Accordingly, the first and second portions are paired together over their range of substantial sequence complementarity, thereby forming the dsRNA molecule. The first and the second RNA strands may be linked to one another, either directly or through an intermediate RNA sequence, and then consist in a single stranded RNA molecule, which becomes a dsRNA by folding on itself while the substantially complementary portions pair together.

Alternatively, the invention may also provide for a RNA molecule comprising i) a first portion having a nucleotide sequence substantially identical to at least 18 contiguous nucleotides of the nucleotide sequence of the mRNA transcribed by a fungal HXT1 gene and ii) a second portion having a nucleotide sequence substantially complementary to the one of the first portion of the first strand. Such RNA molecule has the potential of folding on itself by pairing of its substantially complementary portions, thereby forming a dsRNA molecule.

As used herein, "RNAi" or "RNA interference" refers interchangeably to the process of sequence-specific gene silencing mediated by double-stranded RNA (dsRNA). As used herein, "dsRNA" or "double stranded RNA" refers to RNA molecules that are partially or completely double stranded due to the contiguous nucleotide sequence complementarity between each strand, or certain portions thereof. The process of RNA interference is well described in the literature, and involves in particular the enzyme Dicer, which cuts a long dsRNA molecule into smaller pieces of dsRNA of about 20 nucleotides called microRNA (miRNA) and short-interfering RNA (siRNA). These miRNAs and siRNAs become unpaired and one of the strands interacts with an enzymatic complex called RISC (RNA-Induced Silencing Complex). RISC contains a catalytic enzyme, named Argonaute, which cleaves mRNA molecules having a complementary sequence to the siRNA strand engaged with the RISC, thereby leading to post-transcriptional gene silencing of such mRNA molecules. Double stranded RNA may have different shapes or lengths and may accordingly also be referred to in the literature or by the skilled person with different names, like e.g. small or short interfering RNA (siRNA), short interfering nucleic acid (siNA), micro-RNA (miRNA), circular interfering RNA (ciRNA), or short hairpin RNA (shRNA).

Also as used herein, the terms "nucleic acid" and "polynucleotide" refer to RNA or DNA that is linear, single or double stranded. When dsRNA is produced synthetically, less common bases, such as inosine, 5-methylcytosine, 6-methyladenine, hypoxanthine and others may also be used for improving base pairing. For example, polynucleotides that contain C-5 propyne analogues of uridine and cytidine have been shown to bind RNA with higher affinity than their naturally-occurring equivalent bases, and to be efficient inhibitors of gene expression. Other modifications, such as modification to the phosphodiester backbone, locked nucleic acid or the 2'-hydroxy in the ribose sugar group of the RNA may also be made.

As used herein, the term "substantially identical" or "corresponding to" refers to the sequence identity between either the nucleotide sequences of two polynucleotides or the amino acid sequences of two polypeptides. According to the invention, two polynucleotides have a nucleotide sequence identity of at least 70%, and two polypeptides have an amino acid sequence identity of at least 70%. 70% of nucleotide sequence or amino acid sequence identity means that 70% of the nucleotides of the two polynucleotides, or 70% of the amino acids of the two polypeptides, are identical over the considered length of such polynucleotides, respectively such polypeptides. Preferably, the two polynucleotides or the two polypeptides have a nucleotide sequence identity, respectively an amino acid sequence identity, of at least 75%, 80%, 85%, 90%, 95%, 96%, 97%, 98%, 99% or 100%.

As used herein, the term "substantially identical" as applied to the dsRNA of the invention means that the RNA sequence of one strand of the dsRNA, or a portion thereof, has at least 70%, at least 75%, at least 80%, at least 85%, at least 90% at least 95%, 96%, 97%, 98%, 99% or 100% sequence identity with 18 or more contiguous nucleotides of the mRNA transcribed by the fungal HXT1 gene. "18 or more contiguous nucleotides" means a portion of at least 18, 19, 20, 21, 22, 23, 24, 25, 50, 100, 200, 300, 400, 500, 1000, 1500, or 2000 consecutive bases, or up to the full length of the mRNA transcribed by the fungal HXT1 gene. Accordingly, the length of the portion of substantial sequence identity with the fungal HXT1 gene usually determines the length of the first and second portions of the dsRNA molecule.

As used herein, "complementary" nucleotide sequences refer to two single-stranded nucleotide sequences which nucleotide bases are complementary over a certain contiguous part (or a substantially contiguous part) of their respective sequences according to the standard Watson & Crick complementarity rules, and are therefore capable of pairing or hybridizing with each other over their respective complementary parts. Specifically, purine bases pair with pyrimidines bases, and more specifically a guanine base pairs with a cytosine base (G:C) and an adenine base pairs with either a thymine base (A:T) in the case of DNA, or with a uracil base (A:U) in the case of RNA. It is understood that two polynucleotides may pair or hybridize with each other even if they are not completely complementary with each other, provided that each has at least one region that is substantially complementary to the other, or a sufficient number of complementary bases. As used herein in the context of the present invention, the term "substantially complementary" means that the nucleotide sequences of two polynucleotides of similar length (or portions thereof) are complementary over at least 80% of their respective nucleotides, i.e. they have at least 80% of their respective nucleotides that are capable of pairing or hybridizing with a complementary nucleotide at the corresponding position of the other nucleotide sequence. Preferably, the two polynucleotides have nucleotide sequences that are complementary over at least 85%, 90%, 95%, 96%, 97%, 98%, 99% or more or all of their nucleotides. Alternatively, "substantially complementary" means that two polynucleotides can hybridize under high stringency conditions.

According to the invention, the first strand and the second strand of the dsRNA, or the first and second portions thereof, may have identical sizes. Alternatively, the size of the first strand may be greater than that of the second strand. By way of example, the size of the first strand can be about 200 nucleotides greater than the size of the second strand. In another aspect of the invention, the size of second strand is greater than that of the first strand.

The complementary portions of each RNA strand may be the full length of the RNA strands, and then the base pairing occurs over the whole length of the RNA strands, or they may be shorter than the RNA strands, and then the base pairing occurs only over the portion of sequence complementarity of the RNA strands.

In a particular embodiment of the invention, the fungal HXT1 gene is a rust HXT1 gene.

Accordingly, the invention provides a dsRNA molecule comprising:

i) a first RNA strand comprising a first portion having a nucleotide sequence substantially identical to at least 18 contiguous nucleotides of the nucleotide sequence of the mRNA transcribed by a fungal HXT1 gene and ii) a second RNA strand comprising a second portion having a nucleotide sequence substantially complementary to the one of the first portion of the first strand, wherein said fungal HXT1 gene is a rust HXT1 gene.

A "rust" or "fungal rust" means, in the context of the invention, a plant pathogen of the phylogenic order Pucciniales. Accordingly, a "rust HXT1 gene" is a gene encoding an HXT1 protein and originating from a fungal species of the phylogenic order Pucciniales. Exemplary species of the phylogenic order Pucciniales are *Phakopsora pachyrhizi, Uromyces fabae, Puccinia striiformis, Puccinia triticina* and *Puccinia graminis*. Accordingly, a rust HXT1 gene is a gene originating from, i.e. naturally present in, one of these species. A preferred rust HXT1 gene according to the invention is the HXT1 gene of the species *Phakopsora pachyrhizi*.

In a particular embodiment, the invention provides a dsRNA molecule comprising:

i) a first RNA strand comprising a first portion having a nucleotide sequence substantially identical to at least 18 contiguous nucleotides of the nucleotide sequence of the mRNA transcribed by a fungal rust HXT1 gene and ii) a second RNA strand comprising a second portion having a nucleotide sequence substantially complementary to the one of the first portion of the first strand, wherein said fungal rust HXT1 gene is selected from the list consisting of:

a) a polynucleotide comprising a sequence set forth in SEQ ID NO: 1, 3, 5, 7 and 9;
b) a polynucleotide encoding a polypeptide having a sequence set forth in SEQ ID NO: 2, 4, 6, 8 and 10;
c) a polynucleotide having at least 70% sequence identity to a polynucleotide having a sequence as set forth in SEQ ID NO: 1, 3, 5, 7 and 9;

d) a polynucleotide encoding a polypeptide having at least 70% sequence identity to a polypeptide having a sequence as set forth in SEQ ID NO: 2, 4, 6, 8 and 10;
e) a polynucleotide hybridizing under stringent conditions to a polynucleotide having a sequence as set forth in SEQ ID NO: 1, 3, 5, 7 and 9.

If the polypeptides or polynucleotides that are compared have different lengths, the percentage of sequence identity is to be determined in such a way that the number of respectively amino acids or nucleotides of the shorter sequence that are in common with the longer sequence, determines the length over which the percentage of sequence identity is determined. These computer programs usually use the Needleman and Wunsch global alignment algorithm to align two sequences over their entire length, maximizing the number of matches and minimizing the number of gaps. Generally, the default parameters are used, with a gap creation penalty=10 and gap extension penalty=0.5 (both for nucleotide and protein alignments). Preferably, identity is determined by means of the computer program ClustalW, which is well known and available to the public (Thompson et al., 1994, Nucleic Acids Research 22, 4673-4680). ClustalW is made publicly available on http://www.ebi.ac.uk/tools/clustalW2/index.html. Preferably, Version 2.1 of the ClustalW computer program is used to determine the identity between proteins according to the invention and other proteins. In doing so, the following parameters must be set: KTUPLE=1, TOPDIAG=5, WINDOW=5, PAIRGAP=3, GAPOPEN=10, GAPEXTEND=0.05, GAPDIST=8, MAXDIV=40, MATRIX=GONNET, ENDGAPS(OFF), NOPGAP, NOHGAP. Preferably, Version 2.1 of the ClustalW computer program is used to determine the identity between the nucleotide sequence of the nucleic acid molecules according to the invention, for example, and the nucleotide sequence of other nucleic acid molecules. In doing so, the following parameters must be set: KTUPLE=2, TOPDIAGS=4, PAIRGAP=5, DNAMATRIX:IUB, GAPOPEN=10, GAPEXT=5, MAXDIV=40, TRANSITIONS: unweighted.

According to the present invention, the term 'hybridizing under stringent conditions" refers to conditions under which a polynucleotide hybridizes (usually designed as a probe) to another one with a detectably greater degree than to other polynucleotides (e.g., at least 2-fold over background). Stringent conditions are sequence-dependent and differ according to circumstances. By controlling the stringency of the hybridization and/or washing conditions, polynucleotides that are 100% identical in sequence to a polynucleotide probe can be identified (homologous probing). Alternatively, stringency conditions can be adjusted to allow some mismatching in sequences so that polynucleotides with lower degrees of sequence identity are detected (heterologous probing). Generally, a polynucleotide probe is less than about 1000 nucleotides in length, preferably less than 500 nucleotides in length.

Generally, stringent conditions are selected to be about 5° C. lower than the thermal melting point (Tm) for the specific sequences at a defined ionic strength and pH. The Tm is the temperature (under defined ionic strength and pH) at which 50% of the target sequence hybridizes to a perfectly matching probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions. Stringent conditions for DNA-DNA hybridization (Southern blots using a probe of e.g. 100 nt) are for example those which include at least one wash (usually 2) in 0.2×SSC at a temperature of at least 50° C., usually about 55° C., for 20 min, or equivalent conditions. See also Sambrook et al. (1989) Molecular Cloning: A Laboratory Manual, Second Edition, Cold Spring Harbor Laboratory Press, and Sambrook and Russell (2001) Molecular Cloning: A Laboratory Manual, Third Edition, Cold Spring Harbor Laboratory Press, NY; and in Volumes 1 and 2 of Ausubel et al. (1994) Current Protocols in Molecular Biology, Current Protocols, USA.

Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37'C, and a wash in 0.5× to 1×SSC at 55 to 60° C. Exemplary high stringency conditions include hybridization in 50%>formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Hybridization can be carried out according to the usual methods in the art that are well known to the skilled person (in particular Sambrook et al., 2001, Molecular Cloning: A Laboratory Manual, Third Edition, Cold Spring Harbor Laboratory Press, NY).

In a particular embodiment of the invention, the dsRNA molecule may be applied on the plant or crop to be protected either in a preventive manner (i.e. infection of the plant with a rust fungus has not yet occurred) or in a curative manner (i.e. the plant is already infected with a rust fungus). The present invention therefore also relates to a composition comprising an effective and non-phytotoxic amount of a dsRNA molecule as defined herein.

dsRNA molecules according to the invention may be made by classical chemical synthesis or solid-phase DNA synthesis, by means of in vitro transcription or they may be produced in living organisms like animals cells, bacteria, yeasts, or plants by heterologous (i.e. recombinant) expression (Aalto et al, 2007 RNA 13:422-429.).

The present invention therefore relates to a transgenic organism, preferably a transgenic microorganism, producing a dsRNA molecule as herein defined.

Accordingly, the present invention also relates to a genetic construct comprising at least one DNA molecule as well as heterologous regulatory element(s) in the 5' and, optionally, in the 3' positions, characterized in that the DNA molecule codes for a RNA transcript that can form a dsRNA molecule as herein defined. The present invention also relates to a cloning and/or expression vector, characterized in that it contains at least one such genetic construct.

The expression "effective and non-phytotoxic amount" refers to an amount of composition according to the invention that is sufficient to control or destroy the pathogen present or liable to appear on a crop and which does not entail any appreciable symptom of phytotoxicity for such crop. Such amount can vary within a wide range depending on the pathogen to be controlled, the type of crop, the climatic conditions and the compounds included in the composition according to the invention. This amount can be determined by systematic trials, in greenhouses or in the field, which are within the capabilities of a person skilled in the art.

Thus, there is also provided a composition comprising, as active ingredient, an effective and non-phytotoxic amount of a dsRNA molecule as herein defined and an agriculturally acceptable support, carrier, filler and/or surfactant.

According to the invention, the term "support" denotes a natural or synthetic, organic or inorganic, compound with which the active ingredient, i.e. the dsRNA, is combined or associated to make it easier to apply on the plants. This support is thus generally inert and should be agriculturally acceptable. The support can be a solid or a liquid. Examples of suitable supports include clays, natural or synthetic silicates, silica, resins, waxes, solid fertilizers, water, alcohols, in particular butanol organic solvents, mineral and plant oils and derivatives thereof. Mixtures of such supports can also be used.

The composition according to the invention can also comprise additional components such as, but not limited to, surfactant, protective colloids, adhesives, thickeners, thixotropic agents, penetration agents, stabilizers, sequestering agents. More generally, the active compounds can be combined with any solid or liquid additive, which complies with the usual formulation techniques.

In general, the composition according to the invention can contain from 0.05 to 99% by weight of active ingredient, preferably 10 to 70% by weight.

Compositions according to the invention can be used in various forms such as aerosol dispenser, capsule suspension, cold fogging concentrate, dustable powder, emulsifiable concentrate, emulsion oil in water, emulsion water in oil, encapsulated granule, fine granule, flowable concentrate for seed treatment, gas (under pressure), gas generating product, granule, hot fogging concentrate, macrogranule, microgranule, oil dispersible powder, oil miscible flowable concentrate, oil miscible liquid, paste, plant rodlet, powder for dry seed treatment, seed coated with a pesticide, soluble concentrate, soluble powder, solution for seed treatment, suspension concentrate (flowable concentrate), ultra-low volume (ULV) liquid, ultra-low volume (ULV) suspension, water dispersible granules or tablets, water dispersible powder for slurry treatment, water soluble granules or tablets, water soluble powder for seed treatment and wettable powder. These compositions include not only compositions which are ready to be applied to the plant or seed to be treated by means of a suitable device, such as a spraying or dusting device, but also concentrated commercial compositions which must be diluted before application to the crop.

The dsRNA compounds according to the invention can also be mixed with one or more other plant protection compound or plant growth promoting compound, such as a fungicide, herbicide, insecticide, nematicide, acaricide, molluscicide, resistance inducer, safeners, signal compounds, biologicals, pheromone active substance or other compounds with biological activity. The mixtures thus obtained have a broadened spectrum of activity. Mixtures with other fungicide compounds are particularly advantageous.

According to another particular embodiment of the invention, the dsRNA is introduced or produced into the plant to be protected. After introduction into the plant, the dsRNA may be further processed by the plant cell's RNAi processing machinery into so-called small dsRNA fragments (siRNAs) and may subsequently become distributed throughout the plant, thereby protecting the plant against infections by fungal rust pathogens. The introduced dsRNA may also be processed into siRNAs by the fungal cell's RNAi processing machinery after uptake of the longer dsRNA by the fungal cells.

Alternatively, the dsRNA is produced into the plant by stable or transient genetic transformation of the plant cells with a DNA molecule or genetic construct enabling the expression of the dsRNA in a tissue, temporal, spatial or inducible manner, which may then be further processed into small dsRNA fragments (siRNAs) by a plant cell's RNAi processing machinery. The so produced dsRNA may also be processed into siRNAs by the fungal cell's RNAi processing machinery after uptake of the longer dsRNA by the fungal cells.

Transient genetic transformation may be carried out using recombinant plant viruses in a method known as Virus-Induced Gene Silencing (VIGS). Many VIGS vectors are available to induce transient expression of recombinant DNA or RNA molecules in plants (Purkayastha et al., 2009, Plant Physiol. Biochem. 47: 967-976). A preferred VIGS vector for expressing a dsRNA according to the invention in soybean plants is the Bean Pod Mottle Virus (BPMV; Zhang et al., 2010, Plant Physiol. 153: 52-65).

Accordingly, the invention also relates to a genetic construct or chimeric gene which is able to produce the dsRNA of the invention inside plant cells. Such genetic construct or chimeric gene comprises at least one DNA molecule as well as heterologous regulatory element(s) in the 5' and optionally in the 3' positions which are able to function in plants, characterized in that the DNA molecule is able to form a dsRNA molecule as herein defined once expressed in the plant.

In a particular embodiment, the genetic construct or chimeric gene comprises:

a promoter regulatory element that is functional in plant cells, operably linked to;

a DNA molecule which, when transcribed, generates an RNA molecule comprising, in the direction of transcription, a first portion having a nucleotide sequence in sense direction and a second portion having a nucleotide sequence in antisense direction, said nucleotide sequence of the first portion in sense direction consisting of a nucleotide sequence substantially identical to at least 18 contiguous nucleotides of the mRNA transcribed by a fungal rust HXT1 gene, and said nucleotide sequence of the second portion in antisense direction consisting of a nucleotide sequence substantially complementary, though in antisense direction, to the one of the first portion in sense direction, said substantial complementarity allowing hybridization of the first and second portions of the mRNA molecule together, thereby enabling the formation of a dsRNA, and;

optionally a terminator regulatory element.

Accordingly, the genetic construct or chimeric gene comprises:

a promoter regulatory element functional in plant cells, operably linked to;

a DNA molecule comprising, in the direction of transcription, a first portion having a nucleotide sequence in sense direction and a second portion having a nucleotide sequence in antisense direction, said nucleotide sequence of the first portion in sense direction consisting of a nucleotide sequence substantially identical to at least 18 contiguous nucleotides of the nucleotide sequence of a fungal rust HXT1 gene, and said nucleotide sequence of the second portion in antisense direction consisting of a nucleotide sequence substantially complementary, though in antisense direction, to the one of the first portion in sense direction, and;

optionally, a terminator regulatory element.

"Sense direction" means, for a given DNA molecule to be transcribed or a given RNA molecule, that its nucleotide sequence is orientated in the 5' to 3' direction. "Antisense direction" means that the nucleotide sequence is orientated in the 3' to 5' direction of the DNA or RNA molecule. DNA molecules are usually double-stranded, and each portion to be transcribed on such DNA molecule (e.g. the coding sequence of a gene) has its nucleotide sequence in the sense direction on one of the DNA strands and a complementary nucleotide sequence in the antisense direction on the other strand. In the context of the invention, a DNA molecule designed for being transcribed in an RNA that will form a dsRNA comprises two substantially complementary portions on the same strand, one in the sense direction and its substantially complementary one in the antisense direction. Accordingly, the (single stranded) RNA transcribed from such DNA molecule is made of one single strand comprising both the transcribed portion in the sense direction and its substantially complementary portion in the antisense direction, and can therefore transform in a dsRNA by folding on itself and pairing of the substantially complementary portions.

The DNA sequence of the genetic construct or chimeric gene according to the invention may have several different designs.

According to a first embodiment, the DNA molecule comprises two nucleic acid portions, one having its nucleotide sequence in a sense orientation and one having its nucleotide sequence in an antisense orientation, separated by a spacer or an intron. The nucleic acid portion having its nucleotide sequence in the sense orientation is substantially identical to at least 18 contiguous nucleotides of the nucleotide sequence of a fungal rust HXT1 gene, the nucleic acid portion having its nucleotide sequence in the antisense orientation is substantially complementary to the portion having its nucleotide sequence in the sense orientation, and the spacer or intron does not exhibit any sequence identity with nucleotide sequences of the two other nucleic acid portions. The transcription of such a DNA sequence in a plant cell generates a long single-stranded RNA molecule corresponding to the "sense/spacer (or intron)/antisense" construct. This long RNA transcript can be detected by RT-PCR. Due to the substantial sequence complementarity between the sense and antisense nucleotide sequences of the two RNA portions, they naturally pair or hybridize with one another to form a dsRNA, whereby this dsRNA is a folded RNA and the spacer or intron RNA sequence which separates the two complementary portions forms a loop, thereby leading to the formation of a so-called "hairpin" type of dsRNA. The dsRNA is subsequently degraded by an enzymatic complex "DICER" into small dsRNAs (siRNAs), which are small double-stranded RNAs having a size comprised in the range between 19 and 25 bases. These siRNAs are then processed in the RNAi enzymatic machinery for eventually pairing with the transcribed mRNAs of the fungal HXT1 gene in the fungal cell, thereby leading to their degradation. It is yet unknown though at which stage of this process, and therefore which exact elements (dsRNA, siRNA . . . ), uptake takes place from the plant cells to the fungal cells.

According to another embodiment, the DNA molecule comprises two nucleic acid portions, one having its nucleotide sequences in a sense orientation and one having its nucleotide sequences in an antisense orientation, the two sequences being directly consecutive to one another (i.e. not being separated by any spacer, intron or other nucleic acid element). The nucleic acid portion having its nucleotide sequence in the sense orientation is substantially identical to at least 18 contiguous nucleotides of the nucleotide sequence of a fungal rust HXT1 gene, the nucleic acid portion having its nucleotide sequence in the antisense orientation is substantially complementary to, either part of or more than, the portion having its nucleotide sequence in the sense orientation, the two nucleic acid portions being of different lengths and the extra part of the longest portion comprising a nucleotide sequence that does not exhibit any sequence complementarity with the nucleotide sequence of the other, partially complementary, portion. Accordingly, once the portion in the sense orientation and the one in the antisense orientation hybridize along their complementary portions, a loop structure is formed by the extra part of the longest portion that does not exhibit any sequence complementarity with the other portion. The transcription of such a DNA sequence in a plant cell generates a long single-stranded RNA molecule corresponding to the "sense/antisense" construct. This long RNA transcript can be detected by RT-PCR. Due to the substantial sequence complementarity between the sense and antisense nucleotide sequences of the two RNA portions, they naturally pair or hybridize with one another to form a dsRNA, whereby this dsRNA is a folded RNA and the RNA part corresponding to the extra part of the longest portion forms a loop, thereby also leading to the formation of a so-called "hairpin" type of dsRNA. The dsRNA is subsequently degraded by an enzymatic complex "DICER" into small dsRNAs (siRNAs), which are small double-stranded RNAs having a size comprised in the range between 19 and 25 bases. These siRNAs are then processed in the RNAi enzymatic machinery for eventually pairing with the transcribed mRNAs of the fungal HXT1 gene in the fungal cell, thereby leading to their degradation. It is yet unknown though at which stage of this process, and therefore which exact elements (dsRNA, siRNA . . . ), uptake takes place from the plant cells to the fungal cells.

According to another embodiment, the genetic construct comprises:

two promoter regulatory sequences that are functional in plant cells, wherein the first promoter regulatory sequence is operably linked to a first DNA molecule which, when transcribed, generates a first RNA molecule comprising at least a first nucleic acid portion in a sense direction, and the second promoter regulatory sequence is operably linked to a second DNA molecule which, when transcribed, generates a second RNA molecule comprising at least a second nucleic acid portion in an antisense direction, said second nucleic acid portion being substantially complementary to the first nucleic acid portion, and wherein said first nucleic acid portion in a sense direction comprises a nucleotide sequence substantially identical to at least 18 contiguous nucleotides of the nucleotide sequence of the mRNA transcribed by a fungal rust HXT1 gene, and optionally terminator regulatory sequence(s).

In this particular embodiment, the genetic construct may comprise two chimeric genes, one comprising the first promoter regulatory sequence operably linked to the first DNA molecule which, when transcribed, generates a first RNA molecule comprising at least a first nucleic acid portion in a sense direction which is substantially identical to at least 18 contiguous nucleotides of the nucleotide sequence of the mRNA transcribed by a fungal rust HXT1 gene, and optionally a terminator regulatory sequence, and the second chimeric gene comprising the second promoter regulatory sequence operably linked to the second DNA molecule which, when transcribed, generates a second RNA molecule comprising at least a second nucleic acid portion in an antisense direction, which is substantially complementary to the first nucleic acid portion in the sense direction, and optionally a terminator regulatory sequence.

These two chimeric genes are preferably introduced into the plant cell jointly, but not necessarily, in order to optimize the hybridization of the two single stranded RNA to form the dsRNA.

When genetic constructs are designed with two promoter regulatory sequences, the first and the second promoter regulatory sequences may be different or identical, preferably different.

The invention further relates to a cloning and/or expression vector for transforming a plant, characterized in that it contains at least one chimeric gene or genetic construct as defined herein.

The present invention further relates to a transgenic plant cell comprising a DNA molecule or a genetic construct according to the invention, and therefore expressing a dsRNA molecule of the invention as herein defined.

Among the plants to which the invention may be applied, mention may be made of major field crops like corn (*Zea mays*), soybean (*Glycine max*), cotton (*Gossypium hirsutum*), *Brassica* oilseeds such as *Brassica napus* (e.g. canola), *Brassica rapa*, *B. juncea* (e.g. mustard) and *Brassica carinata*, rice (*Oryza sativa*), wheat (*Triticum* ssp., in particular *Triticum aestivum*), sugar beet (*Beta vulgaris*), sugarcane (*Saccharum Officinarum*), oats (*Avena sativa*), rye (*Secale cereale*), barley (*Hordeum vulgare*), millet, triticale, flax, vine and various fruits and vegetables of various botanical taxa such as *Rosaceae* sp. (for instance pip fruit such as apples and pears, but also stone fruit such as apricots, cherries, almonds and peaches, berry fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for instance banana trees and plantings), *Rubiaceae* sp. (for instance coffee), *Theaceae* sp., *Sterculiceae* sp., *Rutaceae* sp. (for instance lemons, oranges and grapefruit); *Solanaceae* sp. (for instance tomatoes, potatoes, peppers, eggplant), *Liliaceae* sp., *Compositiae* sp. (for instance lettuce, artichoke and chicory—including root chicory, endive or common chicory), *Umbelliferae* sp. (for instance carrot, parsley, celery and celeriac), *Cucurbitaceae* sp. (for instance cucumber—including pickling cucumber, squash, watermelon, gourds and melons), *Alliaceae* sp. (for instance onions and leek), *Cruciferae* sp. (for instance white cabbage, red cabbage, broccoli, cauliflower, brussel sprouts, pak choi, kohlrabi, radish, horseradish, cress, Chinese cabbage), *Leguminosae* sp. (for instance peanuts, peas and beans—such as climbing beans and broad beans), *Chenopodiaceae* sp. (for instance mangold, spinach beet, spinach, beetroots), *Malvaceae* (for instance okra), Asparagaceae (for instance asparagus); horticultural and forest crops; ornamental plants; as well as genetically modified homologues of these crops. The exact plants on which the invention may be applied are plants susceptible of being infected by a fungus comprising an HXT1 gene according to the invention and as defined herein, preferably a rust fungus.

A preferred plant to apply the invention is a soybean plant. Accordingly, in a particular embodiment of the invention, the transgenic plant cell is a soybean plant cell.

The present invention further relates to a transgenic plant, seed or part thereof, comprising transgenic plant cells according to the invention.

In a particular embodiment of the invention, the transgenic plant, seed or part thereof, is a soybean plant, seed or part thereof.

The term "chimeric gene", "genetic construct" or "expression cassette" is generally intended to mean an artificial gene comprising the basic elements of a gene, i.e. a promoter, a coding sequence and a terminator, said elements being derived from at least two different genes as found in nature, and/or from the same gene (i.e. encoding a protein having the same function) of at least two different organisms. A typical "chimeric gene", "genetic construct" or "expression cassette" comprises, functionally linked to one another in the direction of transcription, a promoter regulatory sequence that is functional in plant cells, a DNA sequence capable of being transcribed in a RNA, and, optionally, a terminator that is functional in plant cells.

The expression "chimeric gene", "genetic construct" or "expression cassette" may also encompass sequences encoding a protein or an mRNA that is not directly linked to a promoter regulatory sequence, but is part, for example, of a polycistronic construct comprising several coding sequences under the control of the same promoter regulatory sequence. In such situation, each coding sequences under the control of the promoter regulatory sequence is designed as a "chimeric gene" or "expression cassette".

According to the invention, the expression "functionally linked to one another" means that genetic elements of the chimeric gene are linked to one another in such a way that their function is coordinated and allows the expression of the coding sequence. By way of example, a promoter is functionally linked to a coding sequence when it is capable of ensuring the expression of said coding sequence, i.e. its transcription into a RNA molecule, whether an mRNA (then coding for a protein) or any other type of RNA (e.g. a dsRNA). The construction of the chimeric gene according to the invention and the assembly of its various elements can be carried out using techniques well known to those skilled in the art, in particular those described in Sambrook et al. (2001, Molecular Cloning: A Laboratory Manual, Third Edition, Cold Spring Harbor Laboratory Press, NY). The choice of the regulatory elements constituting the chimeric gene depends essentially on the plant and on the type of cell in which they must function, and those skilled in the art are capable of selecting regulatory elements that are functional in a given plant.

The promoters that the chimeric gene according to the invention may contain may be constitutive or inducible, spatially or temporally regulated.

Among the constitutive promoters that can be used in the chimeric gene of the present invention, mention may be made, by way of example, of bacterial promoters, such as that of the octopine synthase gene or that of the nopaline synthase gene (Sanders et al., 1987, Nucl. Acids Res. 15: 1543-1548), viral promoters, such as that of the gene controlling transcription of the 19S or 35S RNA of the cauliflower mosaic virus (CaMV; Lawton et al., 1987, Plant Mol. Biol. 9: 315-324; Odell et al., 1985, Nature, 313: 810-812), or the promoters of the cassava vein mosaic virus (CsVMV; as described in patent application WO97/48819). Among the promoters of plant origin, mention is made of the promoter of the ribulose-biscarboxylase/oxygenase (RuBisCO) small subunit gene, the promoter of a histone gene as described in application EP 0 507 698, or the promoter of a rice actin gene (Wang et al., 1992, Mol. Cell. Biol., 12: 3399-3406; U.S. Pat. No. 5,641,876).

Among the inducible promoters that can be used in the chimeric gene of the present invention, mention may be made, by way of example, of the promoter of the gene encoding the auxin-binding protein (Schwob et al., 1993, Plant J. 4: 423-432), the promoter of the gene encoding UDP-glucose flavonoid glycosyltransferase (Ralston et al., 1988, Genet., 119: 185-197), the promoter of the gene encoding the MIP proteinase inhibitor (Cordero et al., 1994, Plant J., 6: 141-150), or the promoter of the gene encoding glyceraldehyde-3-phosphate dehydrogenase (Martinez et al., 1989, J. Mol. Biol., 208: 551-565; Quigley et al., 1989, J. Mol. Evol., 29: 412-421; Kohler et al., 1995, Plant Mol. Biol., 29: 1293-1298).

Among the tissue-specific promoters that can be used in the chimeric gene of the present invention, mention may be made, by way of example, of root-specific promoters, such as, for example, that described in patent application WO 00/29594, flower-specific promoters, such as those described in patent applications WO 98/22593, WO 99/15679 or WO 99/43818, or fruit-specific promoters, in particular seed-specific promoters, such as those described in patent applications WO 91/13993, WO 92/17580, WO 98/45460, WO 98/45461 or WO 99/16890.

The term "terminator regulatory sequence" is intended to mean any sequence that is functional in plant cells or plants, also comprising polyadenylation sequences, whether they are of bacterial origin, for instance the nos or ocs terminator of *Agrobacterium tumefaciens*, of viral origin, for instance the CaMV 35S terminator, or else of plant origin, for instance a histone terminator as described in application EP 0 633 317.

The selection step for identifying the transformed cells and/or plants having integrated the construct according to the invention can be carried out by virtue of the presence of a selectable marker gene present in the construct according to the invention or in the plasmid used for the transformation of the cells or of the plants and comprising said construct. The selectable marker gene may be in the form of a chimeric gene comprising the following elements, functionally linked in the direction of transcription: a promoter regulatory sequence that is functional in plant cells, a sequence encoding a selectable marker, and a terminator regulatory sequence that is functional in plant cells.

Among the selectable markers that can be used, mention may be made of markers containing genes for resistance to antibiotics, such as, for example, that of the hygromycin phosphotransferase gene (Gritz et al., 1983, Gene 25: 179-188), of the neomycin phosphotransferase II gene inducing resistance to kanamycin (Wirtz et al., 1987, DNA, 6: 245-253), or of the aminoglycoside 3"-adenyltransferase gene, but also markers containing genes for tolerance to herbicides, such as the bar gene (White et al., 1990, Nucl. Acids Res. 18: 1062) for tolerance to bialaphos, the EPSPS gene (U.S. Pat. No. 5,188,642) for tolerance to glyphosate or else the HPPD gene (WO 96/38567) for tolerance to isoxazoles. Mention may also be made of genes encoding readily identifiable enzymes, such as the GUS enzyme, GFP protein or genes encoding pigments or enzymes regulating pigment production in the transformed cells. Such marker genes are in particular described in patent applications WO 91/02071, WO 95/06128, WO 96/38567, and WO 97/04103.

The present invention further relates to a method of making a transgenic plant cell or plant capable of expressing a dsRNA that triggers inhibition of a fungal rust HXT1 gene, wherein said method comprises the step of transforming a plant cell with a chimeric gene or genetic construct according to the invention.

The method may further comprise the step of selecting the plant cell which has been transformed.

In a particular embodiment of the invention, the invention relates to a method of making a transgenic plant cell or plant capable of expressing a dsRNA as herein described according to the invention, wherein said method comprises the steps of transforming a plant cell with a chimeric gene or genetic construct according to the invention. Preferably, said plant cell is a soybean plant cell or said plant is a soybean plant.

To obtain the cells or plants according to the invention, those skilled in the art can use one of the numerous known methods of transformation.

One of these methods consists in bringing the cells or tissues of the host organisms to be transformed into contact with polyethylene glycol (PEG) and the vectors of the invention (Chang and Cohen, 1979, Mol. Gen. Genet. 168: 111-115; Mercenier and Chassy, 1988, Biochimie 70: 503-517). Electroporation is another method, which consists in subjecting the cells or tissues to be transformed and the vectors of the invention to an electric field (Andreason and Evans, 1988, Biotechniques 6: 650-660; Shigekawa and Dower, 1989, Aust. J. Biotechnol. 3: 56-62). Another method consists in directly injecting the vectors into the cells or the tissues by microinjection (Gordon and Ruddle, 1985, Gene 33: 121-136). Advantageously, the "biolistic" method may be used. It consists in bombarding cells or tissues with particles onto which the vectors of the invention are adsorbed (Bruce et al., 1989, Proc. Natl. Acad. Sci. USA 86: 9692-9696; Klein et al., 1992, Biotechnology 10: 286-291; U.S. Pat. No. 4,945,050). Preferably, the transformation of plant cells or tissues can be carried out using bacteria of the *Agrobacterium* genus, preferably by infection of the cells or tissues of said plants with *A. tumefaciens* (Knopf, 1979, Subcell. Biochem. 6: 143-173; Shaw et al., 1983, Gene 23: 315-330) or *A. rhizogenes* (Bevan and Chilton, 1982, Annu. Rev. Genet. 16: 357-384; Tepfer and Casse-Delbart, 1987, Microbiol. Sci. 4: 24-28). Preferably, the transformation of plant cells or tissues with *Agrobacterium tumefaciens* is carried out according to the protocol described by Hiei et al., (1994, Plant J. 6: 271-282). Those skilled in the art will choose the appropriate method according to the nature of the host organisms to be transformed.

The plants according to the invention contain transformed plant cells as defined above. In particular, the transformed plants can be obtained by regeneration of the transformed plant cells described above. The regeneration is obtained by any appropriate method, which depends on the nature of the plant species.

The present invention also relates to the transformed plants or part thereof, and to plants or part thereof which are derived by cultivating and/or crossing the above regenerated plants, and to the seeds of the transformed plants.

The present invention also relates to end products such as meal, oil or fiber which are obtained from the plants, part thereof, or seeds of the invention.

The invention also comprises parts of these plants, and the progeny of these plants. The term "part of these plants" is intended to mean any organ of these plants, whether above ground or below ground. The organs above ground are the stems, the leaves and the flowers comprising the male and female reproductive organs. The organs below ground are mainly the roots, but they may also be tubers. The term "progeny" is intended to mean mainly the seeds containing the embryos derived from the reproduction of the plants according to the invention with one another. By extension, the term "progeny" applies to all the seeds formed at each new generation derived from crosses between, or with, the transformed plants according to the invention. Progeny and seeds can also be obtained by vegetative multiplication of said transformed plants. The seeds according to the invention can be coated with an agrochemical composition comprising at least one active product having an activity selected from fungicidal, herbicidal, insecticidal, nematicidal, bactericidal or anti-viral activities.

The invention further relates to a method for controlling a plant pathogen, comprising providing to said pathogen a dsRNA molecule according to the invention and as herein defined, or a composition comprising said dsRNA. Preferably, the plant pathogen is a fungal rust.

A fungal rust in the context of the invention is particularly a fungus of the taxonomic order Pucciniales, more specifically of the genius *Puccinia*, preferably *Puccinia graminis*, *Puccinia triticina* or *Puccinia striiformis*, or of the genius *Uromyces*, preferably *Uromyces phaseoli* or *Uromyces appendiculatus*, or of the genius *Phakopsora*, preferably *Phakopsora pachyrhizi*.

The invention also encompasses a method of treatment of plants, preferably crop plants, characterized in that an effective and non-phytotoxic amount of dsRNA molecules according to the invention or of compositions according to the invention is applied to the soil where plants grow or are capable of growing, to the leaves and/or the fruit of plants or to the seeds of such plants.

The invention further relates to a method for controlling a plant, crop or seed pathogen, particularly a fungal rust, characterized in that an agronomically effective and non-phytotoxic amount of dsRNA molecules according to the invention or of compositions according to the invention is applied to the soil where plants grow or are capable of growing, to the leaves and/or the fruit of plants or to the seeds of such plants.

In the context of the invention, applications may be made as seed treatment, foliar application, stem application, drench or drip application (chemigation) to the seed, the plant or the fruit, to the soil or to inert substrate (e.g. inorganic substrates like sand, rockwool, glasswool; expanded minerals like perlite, vermiculite, zeolite or expanded clay), Pumice, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics) wherein the plant is growing or wherein it is desired to be grown.

The invention therefore relates to a method for controlling a plant pathogen, particularly a fungal rust, characterized in that an effective and non-phytotoxic amount of dsRNA molecules according to the invention or of compositions according to the invention is applied to the soil where plants grow or are capable of growing, to the leaves and/or the fruit of plants or to the seeds of such plants.

For the purposes of the present invention, the composition which is the subject of the invention can be applied to the plants by means of various methods of treatment such as:
  spraying onto the aerial parts of the said plants a liquid comprising one of the said compositions,
  dusting, incorporating granules or powders into the soil, spraying, around the said plants and in the case of trees injection or daubing,
  coating or film-coating the seeds of the plants with the aid of a plant-protection mixture comprising one of the said compositions.

The method according to the invention can either be a curing, preventing or eradicating method.

The dose of active dsRNA compound usually applied in the methods of treatment according to the invention is generally and advantageously:
  for foliar treatments: from 0.0001 to 10,000 g/ha, preferably from 0,0001 to 1000 g/ha, more preferably from 0.001 to 300 g/ha; in case of drench or drip application, the dose can even be reduced, especially while using inert substrates like rockwool or perlite;
  for seed treatment: from 0.0001 to 200 g per 100 kilogram of seed, preferably from 0.001 to 150 g per 100 kilogram of seed;
  for soil treatment: from 0.0001 to 10,000 g/ha, preferably from 0.001 to 5,000 g/ha.

The doses herein indicated are given as illustrative examples of method according to the invention. A person skilled in the art will know how to adapt the application doses, notably according to the nature of the plant or crop to be treated.

Under specific conditions, for example according to the nature of the pathogen to be treated or controlled, a lower dose can offer adequate protection. Certain climatic conditions, resistance or other factors like the nature of the pathogen or the degree of infestation, for example, of the plants with these pathogens, can require higher doses of combined active ingredients. The optimum dose usually depends on several factors, for example on the type of pathogen to be treated, on the type or level of development of the infested plant or plant material, on the density of vegetation or alternatively on the method of application.

The dsRNA of the invention may be used in a mixture with another plant protection compound or plant growth promoting compound, said plant protection compound or plant growth promoting compound being used in their dose usually applied.

Such plant protection compound or plant growth promoting compound may be a fungicide, an herbicide, an insecticide, a nematicide, an acaricide, a molluscicide, a resistance inducer, a safener, a biological compound or any other compound having a crop protection activity.

The method of treatment according to the invention can also be useful to treat propagation material such as tubers or rhizomes, but also seeds, seedlings or seedlings pricking out and plants or plants pricking out. This method of treatment can also be useful to treat roots. The method of treatment according to the invention can also be useful to treat the over-ground parts of the plant such as trunks, stems or stalks, leaves, flowers and fruit of the concerned plant, and in general every material which is susceptible to fungal infection (e.g due to storage like hay).

The invention further relates to a method for inhibiting the expression of a plant pathogen, particularly fungal rust, HXT1 gene, comprising the following steps:
i) transforming a plant cell with a chimeric gene according to the invention;
ii) placing the cells thus transformed, or any plants regenerated therefrom, under conditions that allow the transcription of said chimeric gene,
iii) allowing the cells or the plants to be in contact with the pathogen.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and, when introduced in the nuclear, chloroplastic or mitochondrial genome, gives the transformed plant new or improved agronomic or other properties by expressing a protein or polypeptide of interest or by down-regulating or silencing other gene(s) which are present in the plant (using for example, antisense technology, co-suppression technology, RNA interference—RNAi—technology or microRNA—miRNA—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in super-additive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defense system of the plant against attack by unwanted microorganisms. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defense system of plants in such a way that, when subsequently inoculated with unwanted microorganisms, the treated plants display a substantial degree of resistance to these microorganisms. In the present case, unwanted microorganisms are to be understood as meaning phytopathogenic fungi, bacteria and viruses. Thus, the substances according to the invention can be employed for protecting plants against attack by the above mentioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants show a better defense against animal and microbial pests, such as against nematodes, insects, mites, phytopathogenic fungi, bacteria, viruses and/or viroids.

Examples of nematode or insect resistant plants are described in e.g. U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396, 12/497,221, 12/644,632, 12/646,004, 12/701,058, 12/718,059, 12/721,595, 12/638,591.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients, shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigor which results in generally higher yield, vigor, health and resistance towards biotic and abiotic stresses). Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, i.e. the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species (WO 92/05251, WO 95/09910, WO 98/27806, WO 05/002324, WO 06/021972 and U.S. Pat. No. 6,229,072). However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar (e.g. WO 91/02069).

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science 221: 370-371), the CP4 gene of the bacterium *Agrobacterium* sp. (Barry et al., 1992, Curr. Topics Plant Physiol. 7: 139-145), the genes encoding a *Petunia* EPSPS (Shah et al., 1986, Science, 233: 478-481), a Tomato EPSPS (Gasser et al., 1988, J. Biol. Chem. 263: 4280-4289), or an *Eleusine* EPSPS (WO 01/66704). It can also be a mutated EPSPS as described in for example EP 0837944, WO 00/66746, WO 00/66747 or WO 02/26995. Glyphosate-tolerant plants can also be obtained by expressing a gene that encodes a glyphosate oxido-reductase enzyme as described in U.S. Pat. Nos. 5,776,760 and 5,463,175. Glyphosate-tolerant plants can also be obtained by expressing a gene that encodes a glyphosate acetyl transferase enzyme as described in for example WO 02/036782, WO 03/092360, WO 2005/012515 and WO 2007/024782. Glyphosate-tolerant plants can also be obtained by selecting plants containing naturally-occurring mutations of the above-mentioned genes, as described in for example WO 01/024615 or WO 03/013226. Plants expressing EPSPS genes that confer glyphosate tolerance are described in e.g. U.S. patent application Ser. Nos. 11/517,991, 10/739,610, 12/139,408, 12/352,532, 11/312,866, 11/315,678, 12/421,292, 11/400,598, 11/651,752, 11/681,285, 11/605,824, 12/468,205, 11/760,570, 11/762,526, 11/769,327, 11/769,255, 11/943,801 or 12/362,774. Plants comprising other genes that confer glyphosate tolerance, such as decarboxylase genes, are described in e.g. U.S. patent application Ser. Nos. 11/588,811, 11/185,342, 12/364,724, 11/185,560 or 12/423,926.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition, e.g. described in U.S. patent application Ser. No. 11/760,602. One such efficient detoxifying enzyme is an enzyme encoding a phosphinothricin acetyltransferase (such as the bar or pat protein from *Streptomyces* species). Plants expressing an exogenous phosphinothricin acetyltransferase are for example described in U.S. Pat. Nos. 5,561,236; 5,648,477; 5,646,024; 5,273,894; 5,637,489; 5,276,268; 5,739,082; 5,908,810 and 7,112,665.

Further herbicide-tolerant plants are also plants that are made tolerant to the herbicides inhibiting the enzyme hydroxyphenylpyruvatedioxygenase (HPPD). HPPD is an enzyme that catalyze the reaction in which para-hydroxyphenylpyruvate (HPP) is transformed into homogentisate. Plants tolerant to HPPD-inhibitors can be transformed with a gene encoding a naturally-occurring resistant HPPD enzyme, or a gene encoding a mutated or chimeric HPPD enzyme as described in WO 96/38567, WO 99/24585, WO 99/24586, WO 09/144079, WO 02/046387, or U.S. Pat. No. 6,768,044. Tolerance to HPPD-inhibitors can also be obtained by transforming plants with genes encoding certain enzymes enabling the formation of homogentisate despite the inhibition of the native HPPD enzyme by the HPPD-inhibitor. Such plants and genes are described in WO 99/34008 and WO 02/36787. Tolerance of plants to HPPD inhibitors can also be improved by transforming plants with a gene encoding an enzyme having prephenate dehydrogenase (PDH) activity in addition to a gene encoding an HPPD-tolerant enzyme, as described in WO 04/024928. Further, plants can be made more tolerant to HPPD-inhibitor herbicides by adding into their genome a gene encoding an enzyme capable of metabolizing or degrading HPPD inhibitors, such as the CYP450 enzymes shown in WO 2007/103567 and WO 2008/150473.

Still further herbicide resistant plants are plants that are made tolerant to acetolactate synthase (ALS) inhibitors. Known ALS-inhibitors include, for example, sulfonylurea, imidazolinone, triazolopyrimidines, pryimidinyoxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides, as described for example in Tranel and Wright (2002, Weed Science 50: 700-712), but also, in U.S. Pat. Nos. 5,605,011, 5,378,824, 5,141,870, and 5,013,659. The production of sulfonylurea-tolerant plants and imidazolinone-tolerant plants is described in U.S. Pat. Nos. 5,605,011; 5,013,659; 5,141,870; 5,767,361; 5,731,180; 5,304,732; 4,761,373; 5,331,107; 5,928,937; and 5,378,824; and WO 96/33270. Other imidazolinone-tolerant plants are also described in for example WO 2004/040012, WO 2004/106529, WO 2005/020673, WO 2005/093093, WO 2006/007373, WO 2006/015376, WO 2006/024351, and WO 2006/060634. Further sulfonylurea- and imidazolinone-tolerant plants are also described in for example WO 2007/024782 and U.S. Patent Application 61/288,958.

Other plants tolerant to imidazolinone and/or sulfonylurea can be obtained by induced mutagenesis, selection in cell cultures in the presence of the herbicide or mutation breeding as described for example for soybeans in U.S. Pat. No. 5,084,082, for rice in WO 97/41218, for sugar beet in U.S. Pat. No. 5,773,702 and WO 99/057965, for lettuce in U.S. Pat. No. 5,198,599, or for sunflower in WO 01/065922.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:

1) an insecticidal crystal protein from *Bacillus thuringiensis* or an insecticidal portion thereof, such as the insecticidal crystal proteins listed by Crickmore et al. (1998, Microbiology and Molecular Biology Reviews, 62: 807-813), updated by Crickmore et al., "*Bacillus thuringiensis* toxin nomenclature" (2014), http://www.btnomenclature.info/), or insecticidal portions thereof, e.g., proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP-A 1 999 141 and WO 2007/107302), or such proteins encoded by synthetic genes as e.g. described in and U.S. patent application Ser. No. 12/249,016; or 2) a crystal protein from *Bacillus thuringiensis* or a portion thereof which is insecticidal in the presence of a second other crystal protein from *Bacillus thuringiensis* or a portion thereof, such as the binary toxin made up of the Cry34 and Cry35 crystal proteins (Moellenbeck et al., 2001, Nat. Biotechnol. 19: 668-672; Ping et al., 2006, Applied Environm. Microbiol. 71: 1765-1774) or the binary toxin made up of the Cry1A or Cry1F proteins and the Cry2Aa or Cry2Ab or Cry2Ae proteins (U.S. patent application Ser. No. 12/214,022 and EP-A 2 300 618); or 3) a hybrid insecticidal protein comprising parts of different insecticidal crystal proteins from *Bacillus thuringiensis*, such as a hybrid of the proteins of 1) above or a hybrid of the proteins of 2) above, e.g., the Cry1A.105 protein produced by corn event MON89034 (WO 2007/027777); or 4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or 5) an insecticidal secreted protein from *Bacillus thuringiensis* or *Bacillus cereus*, or an insecticidal portion thereof, such as the vegetative insecticidal (VIP) proteins listed at: http://www.lifesci.sussex.ac.uk/home/Neil_Crickmore/Bt/vip.html, e.g., proteins from the VIP3Aa protein class; or 6) a secreted protein from *Bacillus thuringiensis* or *Bacillus cereus* which is insecticidal in the presence of a second secreted protein from *Bacillus thuringiensis* or *Bacillus cereus*, such as the binary toxin made up of the VIP1A and VIP2A proteins (WO 94/21795); or 7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of 5) to 7) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein), such as the VIP3Aa protein in cotton event COT102; or 9) a secreted protein from *Bacillus thuringiensis* or *Bacillus cereus* which is insecticidal in the presence of a crystal protein from *Bacillus thuringiensis*, such as the binary toxin made up of VIP3 and Cry1A or Cry1F (U.S. Patent Applications 61/126,083 and 61/195,019), or the binary toxin made up of the VIP3 protein and the Cry2Aa or Cry2Ab or Cry2Ae proteins (U.S. Patent application Ser. No. 12/214,022 and EP-A 2 300 618).

10) a protein of 9) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation (while still encoding an insecticidal protein)

Of course, an insect-resistant transgenic plant, as used herein, also includes any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected when using different proteins directed at different target insect species, or to delay insect resistance development to the plants by using different proteins insecticidal to the same target insect species but having a different mode of action, such as binding to different receptor binding sites in the insect.

An "insect-resistant transgenic plant", as used herein, further includes any plant containing at least one transgene comprising a sequence producing upon expression a double-stranded RNA which upon ingestion by a plant insect pest inhibits the growth of this insect pest, as described e.g. in WO 2007/080126, WO 2006/129204, WO 2007/074405, WO 2007/080127 and WO 2007/035650.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:

1) plants which contain a transgene capable of reducing the expression and/or the activity of poly(ADP-ribose) polymerase (PARP) gene in the plant cells or plants as described in WO 00/04173, WO 2006/045633, EP-A 1 807 519, or EP-A 2 018 431.

2) plants which contain a stress tolerance enhancing transgene capable of reducing the expression and/or the activity of the PARG encoding genes of the plants or plants cells, as described e.g. in WO 2004/090140.

3) plants which contain a stress tolerance enhancing transgene coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP-A 1 794 306, WO 2006/133827, WO 2007/107326, EP-A 1 999 263, or WO 2007/107326.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behavior, the gelling strength, the starch grain size and/or the starch grain morphology, is changed in comparison with the synthesized starch in wild type plant cells or plants, so that this is better suited for special applications. Said transgenic plants synthesizing a modified starch are disclosed, for example, in EP-A 0 571 427, WO 95/04826, EP-A 0 719 338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO 99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 04/056999, WO 05/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, WO 2008/017518, WO 2008/080630, WO 2008/080631, EP 07090007.1, WO 2008/090008, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. Nos. 5,824,790, 6,013,861, WO 94/04693, WO 94/09144, WO 94/11520, WO 95/35026, WO 97/20936, WO 2010/012796, WO 2010/003701, 2) transgenic plants which synthesize non starch carbohydrate polymers or which synthesize non starch carbohydrate polymers with altered properties in comparison to wild type plants without genetic modification. Examples are plants producing poly-fructose, especially of the inulin and levan-type, as disclosed in EP-A 0 663 956, WO 96/01904, WO 96/21023, WO 98/39460, and WO 99/24593, plants producing alpha-1,4-glucans as disclosed in WO 95/31553, US 2002031826, U.S. Pat. Nos. 6,284,479, 5,712,107, WO 97/47806, WO 97/47807, WO 97/47808 and WO 00/14249, plants producing alpha-1,6 branched alpha-1,4-glucans, as disclosed in WO 00/73422, plants producing alternan, as disclosed in e.g. WO 00/47727, WO 00/73422, EP 06077301.7, U.S. Pat. No. 5,908,975 and EP-A 0 728 213, 3) transgenic plants which produce hyaluronan, as for example disclosed in WO 2006/032538, WO 2007/039314, WO 2007/039315, WO 2007/039316, JP-A 2006-304779, and WO 2005/012529.

4) transgenic plants or hybrid plants, such as onions with characteristics such as 'high soluble solids content', 'low pungency' (LP) and/or 'long storage' (LS), as described in U.S. patent application Ser. No. 12/020,360 and 61/054,026.

Plants or plant cultivars (that can be obtained by plant biotechnology methods such as genetic engineering) which may also be treated according to the invention are plants, such as cotton plants, with altered fiber characteristics. Such plants can be obtained by genetic transformation, or by selection of plants contain a mutation imparting such altered fiber characteristics and include:

a) Plants, such as cotton plants, containing an altered form of cellulose synthase genes as described in WO 98/00549.
b) Plants, such as cotton plants, containing an altered form of rsw2 or rsw3 homologous nucleic acids as described in WO 2004/053219.
c) Plants, such as cotton plants, with increased expression of sucrose phosphate synthase as described in WO 01/17333.
d) Plants, such as cotton plants, with increased expression of sucrose synthase as described in WO 02/45485.
e) Plants, such as cotton plants, wherein the timing of the plasmodesmatal gating at the basis of the fiber cell is altered, e.g. through downregulation of fiber-selective β-1,3-glucanase as described in WO 2005/017157, or as described in WO 2009/143995.
f) Plants, such as cotton plants, having fibers with altered reactivity, e.g. through the expression of N-acetylglucosaminetransferase gene including nodC and chitin synthase genes as described in WO 2006/136351.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation, or by selection of plants that contain a mutation imparting such altered oil profile characteristics and include:

a) Plants, such as oilseed rape plants, producing oil having a high oleic acid content as described e.g. in U.S. Pat. No. 5,969,169, 5,840,946 or 6,323,392 or 6,063,947
b) Plants such as oilseed rape plants, producing oil having a low linolenic acid content as described in U.S. Pat. No. 6,270,828, 6,169,190, or 5,965,755
c) Plant such as oilseed rape plants, producing oil having a low level of saturated fatty acids as described e.g. in U.S. Pat. No. 5,434,283 or U.S. patent application Ser. No. 12/668,303

Plants or plant cultivars (that can be obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants contain a mutation imparting such altered seed shattering characteristics and include plants such as oilseed rape plants with delayed or reduced seed shattering as described in U.S. Patent Application 61/135,230, WO 2009/068313 and WO 2010/006732.

Plants or plant cultivars (that can be obtained by plant biotechnology methods such as genetic engineering) which may also be treated according to the invention are plants, such as Tobacco plants, with altered post-translational protein modification patterns, for example as described in WO 2010/121818 and WO 2010/145846.

Particularly useful transgenic plants which may be treated according to the invention are plants containing transformation events, or combination of transformation events, that are the subject of petitions for non-regulated status, in the United States of America, to the Animal and Plant Health Inspection Service (APHIS) of the United States Department of Agriculture (USDA) whether such petitions are granted or are still pending. At any time this information is readily available from APHIS (4700 River Road, Riverdale, Md. 20737, USA), for instance on its internet site (URL http://www.aphis.usda.gov/brs/not_reg.html). On the filing date of this application the petitions for nonregulated status that were pending with APHIS or granted by APHIS were those which contains the following information:

Petition: the identification number of the petition. Technical descriptions of the transformation events can be found in the individual petition documents which are obtainable from APHIS, for example on the APHIS website, by reference to this petition number. These descriptions are herein incorporated by reference.

Extension of Petition: reference to a previous petition for which an extension is requested.

Institution: the name of the entity submitting the petition.

Regulated article: the plant species concerned.

Transgenic phenotype: the trait conferred to the plants by the transformation event.

Transformation event or line: the name of the event or events (sometimes also designated as lines or lines) for which nonregulated status is requested.

APHIS documents: various documents published by APHIS in relation to the Petition and which can be requested with APHIS.

Additional particularly useful plants containing single transformation events or combinations of transformation events are listed for example in the databases from various national or regional regulatory agencies (see for example http://gmoinfo.jrc.it/gmp_browse.aspx and http://www.agbios.com/dbase.php).

Particularly useful transgenic plants which may be treated according to the invention are plants containing transformation events, or a combination of transformation events, and that are listed for example in the databases for various national or regional regulatory agencies including Event 1143-14A (cotton, insect control, not deposited, described in WO 2006/128569); Event 1143-51B (cotton, insect control, not deposited, described in WO 2006/128570); Event 1445 (cotton, herbicide tolerance, not deposited, described in US-A 2002-120964 or WO 02/034946); Event 17053 (rice, herbicide tolerance, deposited as PTA-9843, described in WO 2010/117737); Event 17314 (rice, herbicide tolerance, deposited as PTA-9844, described in WO 2010/117735); Event 281-24-236 (cotton, insect control—herbicide tolerance, deposited as PTA-6233, described in WO 2005/103266 or US-A 2005-216969); Event 3006-210-23 (cotton, insect control—herbicide tolerance, deposited as PTA-6233, described in US-A 2007-143876 or WO 2005/103266); Event 3272 (corn, quality trait, deposited as PTA-9972, described in WO 2006/098952 or US-A 2006-230473); Event 40416 (corn, insect control—herbicide tolerance, deposited as ATCC PTA-11508, described in WO 2011/075593); Event 43A47 (corn, insect control—herbicide tolerance, deposited as ATCC PTA-11509, described in WO 2011/075595); Event 5307 (corn, insect control, deposited as ATCC PTA-9561, described in WO 2010/077816); Event ASR-368 (bent grass, herbicide tolerance, deposited as ATCC PTA-4816, described in US-A 2006-162007 or WO 2004/053062); Event B16 (corn, herbicide tolerance, not deposited, described in US-A 2003-126634); Event BPS-CV127-9 (soybean, herbicide tolerance, deposited as NCIMB No. 41603, described in WO 2010/080829); Event CE43-67B (cotton, insect control, deposited as DSM ACC2724, described in US-A 2009-217423 or WO2006/128573); Event CE44-69D (cotton, insect control, not deposited, described in US-A 2010-0024077); Event CE44-69D (cotton, insect control, not deposited, described in WO 2006/128571); Event CE46-02A (cotton, insect control, not deposited, described in WO 2006/128572); Event COT102 (cotton, insect control, not deposited, described in US-A 2006-130175 or WO 2004/039986); Event COT202 (cotton, insect control, not deposited, described in US-A 2007-067868 or WO 2005/054479); Event COT203 (cotton, insect control, not deposited, described in WO 2005/054480); Event DAS40278 (corn, herbicide tolerance, deposited as ATCC PTA-10244, described in WO 2011/022469); Event DAS-59122-7 (corn, insect control—herbicide tolerance, deposited as ATCC PTA 11384, described in US-A 2006-070139); Event DAS-59132 (corn, insect control—herbicide tolerance, not deposited, described in WO 2009/100188); Event DAS68416 (soybean, herbicide tolerance, deposited as ATCC PTA-10442, described in WO 2011/066384 or WO 2011/066360); Event DP-098140-6 (corn, herbicide tolerance, deposited as ATCC PTA-8296, described in US-A 2009-137395 or WO 2008/112019); Event DP-305423-1 (soybean, quality trait, not deposited, described in US-A 2008-312082 or WO 2008/054747); Event DP-32138-1 (corn, hybridization system, deposited as ATCC PTA-9158, described in US-A 2009-0210970 or WO 2009/103049); Event DP-356043-5 (soybean, herbicide tolerance, deposited as ATCC PTA-8287, described in US-A 2010-0184079 or WO 2008/002872); Event EE-1 (brinjal, insect control, not deposited, described in WO 2007/091277); Event FI117 (corn, herbicide tolerance, deposited as ATCC 209031, described in US-A 2006-059581 or WO 98/044140); Event GA21 (corn, herbicide tolerance, deposited as ATCC 209033, described in US-A 2005-086719 or WO 98/044140); Event GG25 (corn, herbicide tolerance, deposited as ATCC 209032, described in US-A 2005-188434 or WO 98/044140); Event GHB119 (cotton, insect control—herbicide tolerance, deposited as ATCC PTA-8398, described in WO 2008/151780); Event GHB614 (cotton, herbicide tolerance, deposited as ATCC PTA-6878, described in US-A 2010-050282 or WO 2007/017186); Event GJ11 (corn, herbicide tolerance, deposited as ATCC 209030, described in US-A 2005-188434 or WO 98/044140); Event GM RZ13 (sugar beet, virus resistance, deposited as NCIMB-41601, described in WO 2010/076212); Event H7-1 (sugar beet, herbicide tolerance, deposited as NCIMB 41158 or NCIMB 41159, described in US-A 2004-172669 or WO 2004/074492); Event JOPLIN1 (wheat, disease tolerance, not deposited, described in US-A 2008-064032); Event LL27 (soybean, herbicide tolerance, deposited as NCIMB41658, described in WO 2006/108674 or US-A 2008-320616); Event LL55 (soybean, herbicide tolerance, deposited as NCIMB 41660, described in WO 2006/108675 or US-A 2008-196127); Event LLcotton25 (cotton, herbicide tolerance, deposited as ATCC PTA-3343, described in WO 03/013224 or US-A 2003-097687); Event LLRICE06 (rice, herbicide tolerance, deposited as ATCC-23352, described in U.S. Pat. No. 6,468,747 or WO 00/026345); Event LLRICE601 (rice, herbicide tolerance, deposited as ATCC PTA-2600, described in US-A 2008-2289060 or WO 00/026356); Event LY038 (corn, quality trait, deposited as ATCC PTA-5623, described in US-A 2007-028322 or WO 2005/061720); Event MIR162 (corn, insect control, deposited as PTA-8166, described in US-A 2009-300784 or WO 2007/142840); Event MIR604 (corn, insect control, not deposited, described in US-A 2008-167456 or WO 2005/103301); Event MON15985 (cotton, insect control, deposited as ATCC PTA-2516, described in US-A 2004-250317 or WO 02/100163); Event MON810 (corn, insect control, not deposited, described in US-A 2002-102582); Event MON863 (corn, insect control, deposited as ATCC PTA-2605, described in WO 2004/011601 or US-A 2006-095986); Event MON87427 (corn, pollination control, deposited as ATCC PTA-7899, described in WO 2011/062904); Event MON87460 (corn, stress tolerance, deposited as ATCC PTA-8910, described in WO 2009/111263 or US-A 2011-0138504); Event MON87701 (soybean, insect control, deposited as ATCC PTA-8194, described in US-A 2009-130071 or WO 2009/064652); Event MON87705 (soybean, quality trait—herbicide tolerance, deposited as ATCC PTA-9241, described in US-A 2010-0080887 or WO 2010/037016); Event MON87708 (soybean, herbicide tolerance, deposited as ATCC PTA9670, described in WO 2011/034704); Event MON87754 (soybean, quality trait, deposited as ATCC PTA-9385, described in WO 2010/024976); Event MON87769 (soybean, quality trait, deposited as ATCC PTA-8911, described in US-A 2011-0067141 or WO 2009/102873); Event MON88017 (corn, insect control—herbicide tolerance, deposited as ATCC PTA-5582, described in US-A 2008-028482 or WO 2005/059103); Event MON88913 (cotton, herbicide tolerance, deposited as ATCC PTA-4854, described in WO 2004/072235 or US-A 2006-059590); Event MON89034 (corn, insect control, deposited as ATCC PTA-7455, described in WO 2007/140256 or US-A 2008-260932); Event MON89788 (soybean, herbicide tolerance, deposited as ATCC PTA-6708, described in US-A 2006-282915 or WO 2006/130436); Event MS11 (oilseed rape, pollination control—herbicide tolerance, deposited as ATCC PTA-850 or PTA-2485, described in WO 01/031042); Event MS8 (oilseed rape, pollination control—herbicide tolerance, deposited as ATCC PTA-730, described in WO 01/041558 or US-A 2003-188347); Event NK603 (corn, herbicide tolerance, deposited as ATCC PTA-2478, described in US-A 2007-292854); Event PE-7 (rice, insect control, not deposited, described in WO 2008/114282); Event RF3 (oilseed rape, pollination control—herbicide tolerance, deposited as ATCC PTA-730, described in WO 01/041558 or US-A 2003-188347); Event RT73 (oilseed rape, herbicide tolerance, not deposited, described in WO 02/036831 or US-A 2008-070260); Event T227-1 (sugar beet, herbicide tolerance, not deposited, described in WO 02/44407 or US-A 2009-265817); Event T25 (corn, herbicide tolerance, not deposited, described in US-A 2001-029014 or WO 01/051654); Event T304-40 (cotton, insect control—herbicide tolerance, deposited as ATCC PTA-8171, described in US-A 2010-077501 or WO 2008/122406); Event T342-142 (cotton, insect control, not deposited, described in WO 2006/128568); Event TC1507 (corn, insect control—herbicide tolerance, not deposited, described in US-A 2005-039226 or WO 2004/099447); Event VIP1034 (corn, insect control—herbicide tolerance, deposited as ATCC PTA-3925., described in WO 03/052073), Event 32316 (corn, insect control-herbicide tolerance, deposited as PTA-11507, described in WO 2011/084632), Event 4114 (corn, insect control-herbicide tolerance, deposited as PTA-11506, described in WO 2011/084621).

The composition according to the invention can also be used against fungal diseases liable to grow on or inside timber. The term "timber" means all types of species of wood and all types of working of this wood intended for construction, for example solid wood, high-density wood, laminated wood and plywood. The method for treating timber according to the invention mainly consists in contacting one or more compounds according to the invention or a composition according to the invention; this includes for example direct application, spraying, dipping, injection or any other suitable means.

SEQUENCE LISTING

Figure 1:
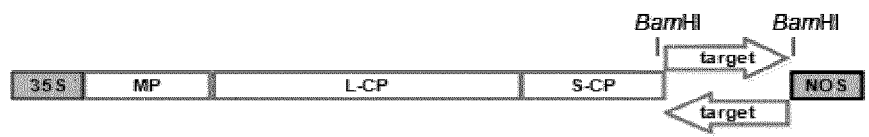
FIG. 1: pBPMV expression cassette (Zhang et al. 2010, Plant Physioloy, 153: 52-65). 35S: CaMV 35S-Promotor: MP: movement protein, L-CP: large coat protein, S-CP: small coat protein, BamHI: BamHI restriction sites, target: target gene fragment, NOS: nopaline synthase terminator.

SEQ ID NO: 1: Nucleotide sequence of the gene encoding the HXT1 protein of Phakopsora pachyrhizi SEQ ID NO: 2: Amino acid sequence of the HXT1 protein of Phakopsora pachyrhizi
SEQ ID NO: 3: Nucleotide sequence of the gene encoding the HXT1 protein of Uromyces fabae
SEQ ID NO: 4: Amino acid sequence of the HXT1 protein of Uromyces fabae
SEQ ID NO: 5: Nucleotide sequence of the gene encoding the HXT1 protein of Puccinia striiformis
SEQ ID NO: 6: Amino acid sequence of the HXT1 protein of Puccinia striiformis
SEQ ID NO: 7: Nucleotide sequence of the gene encoding the HXT1 protein of Puccinia graminis
SEQ ID NO: 8: Amino acid sequence of the HXT1 protein of Puccinia graminis
SEQ ID NO: 9: Nucleotide sequence of the gene encoding the HXT1 protein of Puccinia triticina
SEQ ID NO: 10: Amino acid sequence of the HXT1 protein of Puccinia triticina The various aspects of the invention will be understood more fully by means of the experimental examples below. All the methods or operations described below are given by way of example and correspond to a choice, made among the various methods available for achieving the same result. This choice has no effect on the quality of the result, and, consequently, any appropriate method can be used by those skilled in the art to achieve the same result. In particular, and unless otherwise specified in the examples, all the recombinant DNA techniques employed are carried out according to the standard protocols described in Sambrook and Russel (2001, Molecular cloning: A laboratory manual, Third edition, Cold Spring Harbor Laboratory Press, NY) in Ausubel et al. (1994, Current Protocols in Molecular Biology, Current protocols, USA, Volumes 1 and 2), and in Brown (1998, Molecular Biology LabFax, Second edition, Academic Press, UK). Standard materials and methods for plant molecular biology are described in Croy R. D. D. (1993, Plant Molecular Biology LabFax, BIOS Scientific Publications Ltd (UK) and Blackwell Scientific Publications (UK)). Standard materials and methods for PCR (Polymerase Chain Reaction) are also described in Dieffenbach and Dveksler (1995, PCR Primer: A laboratory manual, Cold Spring Harbor Laboratory Press, NY) and in McPherson et al. (2000, PCR—Basics: From background to bench, First edition, Springer Verlag, Germany).

EXAMPLES

Example 1: Identification of the HXT1 Gene of Phakopsora pachyrhizi

To obtain the Phakopsora pachyrhizi ortholog of HXT1, an annotated haustorial transcriptome generated by Link et al. (2013, Molecular Plant Pathology, 15:379-93) was searched for hexose transporter orthologs. One candidate hexose transporter, contig_05320, exhibited homology to U. fabae HXT1 as well as to candidate hexose transporters from Puccinia graminis f. sp. Tritici and Melampsora larici-populina. Reciprocal BLAST searches using U. fabae genome data (Link et al. 2014, Frontiers in Plant Science, 29; 5:587) confirmed contig_05320 to be the closest homolog to U. fabae HXT1.

Example 2: Vector Construction for VIGS

For VIGS to be successful, it is necessary to use a virus system which has been well established on the host plant. For soybean, Bean Pod Mottle Virus (BPMV) has been established for both VIGS and transient expression of foreign genes (Zhang et al., 2010, Plant Physiology, 153: 52-65). Similarly to the approach of Panwar et al. (2013, Plant Molecular Biology, 81: 595-608), who used an already established vector (BSMV), we chose to adapt the BPMV system for VIGS.

Our BPMV silencing plasmid vector contains a BamHI cloning site between the sequence coding for the small coat protein and the terminator sequence (FIG. 1). For silencing constructs, RT-PCR with specific primers on the HXT1 gene of *P. pachyrhizi* was performed on RNA prepared from infected plant material, and the PCR products were inserted into the BamHI site. Plasmids are then transformed into *E. coli* DH5a for amplification using electroporation. Since cloning into the pBPMV plasmid is not directional, the orientation of the insert is tested using colony PCR. Correct constructs are also sequenced. Both constructs—with the insert in sense and antisense direction—are used for silencing experiments.

The BPMV genome consists of two positively stranded RNAs, of which RNA2 is utilized for cloning. For plant inoculation, three plasmids containing BPMV RNA1 (soybean mosaic virus for boosting the infection), and the silencing construct are simultaneously delivered into soybean primary leaves using particle bombardment.

For particle bombardment, 11-day-old seedlings (primary leaves fully developed, but no further development) are transferred into the vacuum chamber of the biolistic device and leaves supported by a plastic tray with a notch for the stem. Leaves are weighed down flat on the tray with a metal mesh. We are using 1.0 μm gold particles, 1,100-psi rupture disks and a distance of 6 cm. The chamber is evacuated to −25 in Hg prior to particle bombardment. Afterwards, plants are moistened and kept under 100% humidity overnight and later put to standard greenhouse conditions with 22° C. and 16 h light.

Leaves with heavy viral infection were harvested and the sap was used for secondary rubbing inoculation of further plants. Trifoliate leaves of these plants were subsequently inoculated with *P. pachyrhizi* urediospores.

Example 3: Measurement of Expression Levels of HXT1 Gene

For assessing the silencing effect, plants are inoculated with virus by rubbing the primary leaves when they are fully developed. For every screen, 20 plants are used with the silencing construct, 5 with the empty vector, and 3 as non-infected control. Plants are kept in the greenhouse in a randomized distribution. Once the third trifoliate leaf is fully developed, the leaflets of the second and third trifoliate leaves are spray inoculated with *P. pachyrhizi* urediospores. We are using a suspension consisting of 2 mg/ml spores with traces of milk powder and Tween20 added for better dispersion. Plants are kept at 100% humidity in the dark for 24 h—afterwards they are returned to the normal greenhouse regime. Five days post rust inoculation, RNA is prepared for qPCR. One leaflet of either the $2^{nd}$ or $3^{rd}$ trifoliate leaf is chosen and 100 mg leaf material is used for RNA preparation using the Plant RNA Isolation Kit from Agilent (Waldbronn). RNA concentration is measured using fluorimetry (Qubit 2.0, Thermo Fisher Scientific, Life Technologies, Waltham). qPCR for every sample is measured in duplicate. The qPCR-chemistry we are using is the SensiFast SYBR no-Rox Kit (Bioline GmbH, Luckenwalde).

qPCR results are normalized against Pp_RPS14. All samples are first evaluated separately and then the average of all plants is used to determine if silencing was successful. The significance of the silencing effect is determined by standard t-test. All statistical analyses concerning qPCR results are performed using REST-2009 software (Pfaffl 2001, Nucleic Acids Research, 29:e45.

Remaining leaflets are used for symptom assessment.

Figure 2A:
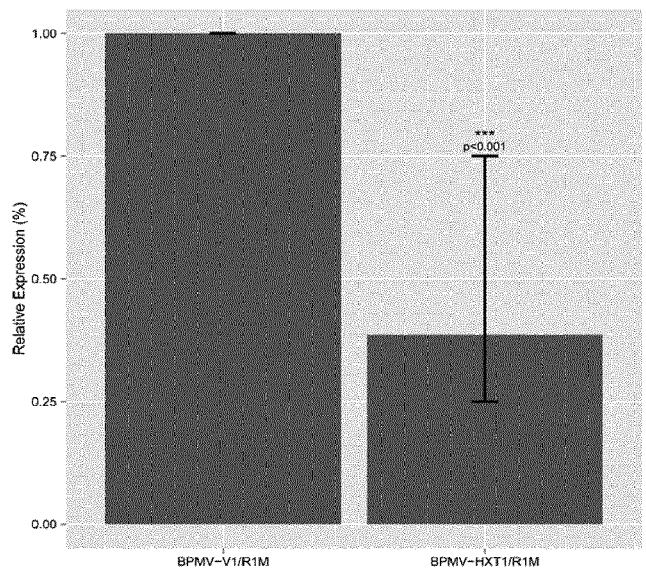
FIG. 2A: Expression level of HXT1 in P. pachyrhizi on plants injected with the HXT1 silencing construct (BPMV-HXT1/R1M) compared to BPMV empty vector (BPMV-V1/R1M). Mean of 13 plants +/−standard error.

Both reduced transcript levels (FIG. 2A) and reduced fungal infection was observed for the HXT1 gene. A phenotypic symptom assessment of the disease (according to the diagrammatic scale of assessment of *Phakopsora pachyrhizi* described in Godoy et al., 2006, Fitopatologia Brasileira 31:63-68) carried out 10 days post-infection showed that, while plants infected with a BPMV empty vector show leaf symptoms close to 60%, the plants infected with the BPMV vector containing the HXT1 silencing construct have developed only about 5% of leaf symptoms.

Figure 2B:
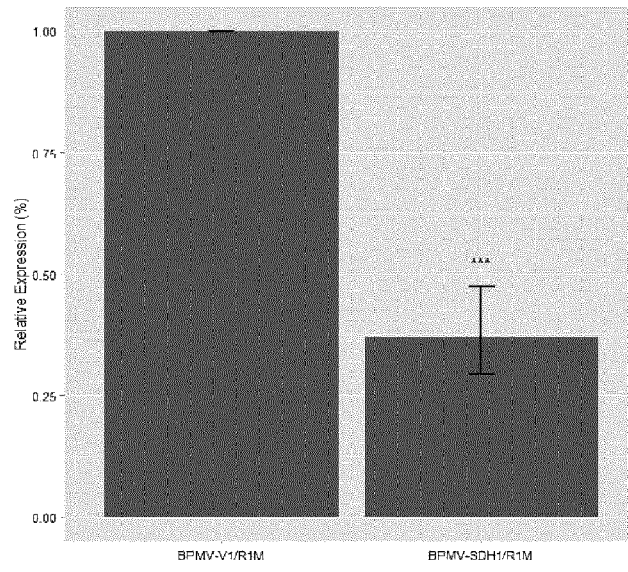
FIG. 2B: Expression level of SDH1 in P. pachzyhizi on plants infected with the SDH1 silencing construct (BPMV-SDH1/R1M) compared to BPMV empty vector (BPMV-V1/R1M). Mean of 12 plants +/−standard error.

By contrast, when VIGS was assayed using a different *P. pachyrhizi* target gene (SDH1), no reduction on *P. pachyrhizi* infection was observed compared to controls (empty BPMV vectors) despite reduced transcript levels (FIG. 2B).

Example 4: Identification of a Rust-Specific Group of HXT1 Proteins

Based on the sequence of the HXT1 protein of *P. pachyrhizi*, homologous sequences have been identified in other species using the BLAST sequence alignment tool.

Percentages of sequence identity between these homologous sequences are shown in Table 1.

These homologous HXT1 proteins show a greater percentage of sequence identity amongst themselves than with other class of hexose transporters, including with the proposed "HXT1-homologue" identified by Yin et al. (2011, MPMI 24: 554-561), thereby indicating that these hexose transporters form a group of homologous HXT1 proteins, sufficiently distinct from other types of hexose transporters. Moreover, these HXT1 proteins find no homologous proteins in other fungi than rusts, thereby indicating that this group of homologous HXT1 proteins is specific to rusts.

TABLE 1

Percentages of sequence identity between hexose transporter proteins of rusts

| | PUCT-R_PTT-G_02739 | PUCG-R_PGT-G_15147 | PUCS-T_PST-G_030803 | PHAKP-A_c17-351 | CRYN-E_CNA-G_04931 | PHAKP-A_c170-24 | UROF-A_14348-970 | PUCG-R_GTG_1-8584 | PUCS-T_PST-G_00917 | PUCT-R_PTT-G_05441 | USTIM-A_um0-5023 |
|---|---|---|---|---|---|---|---|---|---|---|---|
| PUCTR_PTT-G_02739 | 100 | 91.7 | 90.6 | 74.2 | 44.4 | 55.8 | 60.2 | 56.9 | 60.2 | 60.9 | 49.3 |
| PUCG-R_PGT-G_15147 | | 100 | 91.9 | 75 | 44.7 | 55.1 | 60 | 56.5 | 59.8 | 60.9 | 48.9 |

TABLE 1-continued

Percentages of sequence identity between hexose transporter proteins of rusts

| | PUCTR_PTT-G_02739 | PUCGR_PGT-G_15147 | PUCST_PST-G_030803 | PHAKPA_c17-351 | CRYNE_CNA-G_04931 | PHAKPA_c170-24 | UROFA_14348-970 | PUCGR_GTG_1-8584 | PUCST_PST-G_00917 | PUCTR_PTT-G_05441 | USTIMA_um0-5023 |
|---|---|---|---|---|---|---|---|---|---|---|---|
| PUCS-T_PST-G_03803 | | | 100 | 75.5 | 44.5 | 55.3 | 61.1 | 56.7 | 60.5 | 61.5 | 49.3 |
| PHAKP-A_c17351 | | | | 100 | 43.7 | 54.4 | 60.3 | 55.5 | 60.1 | 60.8 | 48.5 |
| CRY-NE_CNA-G_04931 | | | | | 100 | 46.1 | 42.7 | 40.9 | 43.3 | 43.2 | 36.6 |
| PHAKP-A_c17024 | | | | | | 100 | 72 | 68.3 | 72.3 | 73.6 | 46.5 |
| UROF-A_14348-970 | | | | | | | 100 | 86.8 | 91.2 | 92 | 47.2 |
| PUCG-R_PGT-G_18584 | | | | | | | | 100 | 88.8 | 90.2 | 44.5 |
| PUCST_P-STG_009-17 | | | | | | | | | 100 | 93.7 | 48.6 |
| PUCT-R_PTT-G_05441 | | | | | | | | | | 100 | 47.5 |

PHAKPA: *Phakopsora pachyrhizi*
UROFA: *Uromyces fabae*
PUCGR: *Puccinia graminis*
PUCST: *Puccinia striiformis* (Note: "PUCST PSTG 03803" is the "HXT1-homologue" identified by Yin et al. (2011, MPMI 24: 554-561)
PUCTR: *Puccinia triticina*
CRYNE: *Cryptococcus neoformans*
USTIMA: *Ustilago maydis*

Figure 3:
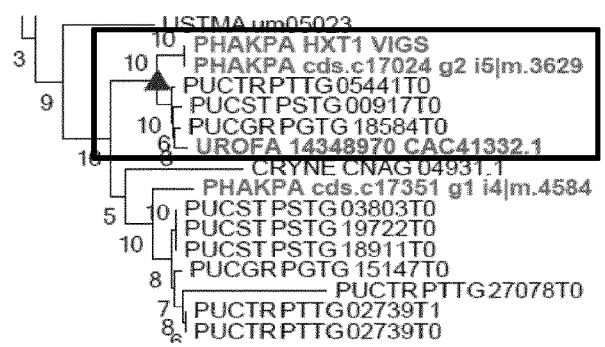
FIG. 3: A phylogenetic tree including rust-specific HXT1-proteins.

Based on sequence alignments, also including hexose transporter proteins from other fungi, a phylogenetic tree was build (FIG. 3). Alignments were performed on ClustalW2 with the matrix Blosum, a gap extension fixed at 0.05 and a gap open penalty of 10. The phylogenic tree was generated with Phyml (Guindon et al. (2010), Systematic Biology, 59(3):307-21) with default parameters and 10 bootstraps. The homologous HXT1 proteins are grouped on a single branch of the phylogenetic tree, thereby confirming some specificity of these HXT1 proteins among rust species.

The invention claimed is:

1. A dsRNA molecule comprising:
   i) a first RNA strand comprising a first portion having a nucleotide sequence identical to at least 18 contiguous nucleotides of the nucleotide sequence of the mRNA transcribed by a fungal HXT1 gene; and
   ii) a second RNA strand comprising a second portion having a nucleotide sequence substantially complementary to the one of the first portion of the first strand, such that the first and second portions are able to pair together over their range of substantial sequence complementarity,
   wherein the fungal HXT1 gene is:
   a) a polynucleotide comprising a nucleotide sequence asset forth in SEQ ID NO:1, 5, 7 and 9; or
   b) a polynucleotide encoding a polypeptide having an amino acid sequence as set forth in SEQ ID NO: 2, 6, 8 and 10, and
   wherein the dsRNA molecule inhibits expression of a *Phakopsora* HXT1 gene and is capable of treating or protecting plants from fungal rusts of the order of Pucciniales.

2. A composition comprising at least an effective and non-phytotoxic amount of a dsRNA molecule according to claim 1.

3. An expression cassette or genetic construct comprising at least:

i) a promoter regulatory element functional in plant cells, operably linked to ii) a DNA molecule comprising, in the direction of transcription, a first portion having a nucleotide sequence in sense direction and a second portion having a nucleotide sequence in antisense direction, said nucleotide sequence of the first portion in sense direction consisting of a nucleotide sequence identical to at least 18 contiguous nucleotides of the nucleotide sequence of a fungal HXT1 gene, and said nucleotide sequence of the second portion in antisense direction consisting of a nucleotide sequence substantially complementary to the one of the first portion in sense direction; and iii) optionally, a terminator regulatory element, wherein the fungal HXT1 gene is:

a) a polynucleotide comprising a nucleotide sequence as set forth in SEQ ID NO:1, 5, 7 and 9; or b) a polynucleotide encoding a polypeptide having an amino acid sequence as set forth in SEQ ID NO: 2, 6, 8 and 10, and wherein the DNA molecule inhibits expression of a *Phakopsora* HXT1 gene and is capable of treating or protecting plants from fungal rusts of the order of Pucciniales.

4. A transgenic organism comprising at last one expression cassette or genetic construct according to claim 3.

5. The transgenic organism according to claim 4, wherein said organism is a plant cell, or a plant, or a seed, or a part thereof.

6. The transgenic plant cell, plant, seed or part thereof, according to claim 5, wherein said plant is a soybean plant, seed or part thereof.

7. A method for making a transgenic plant cell, plant, seed or part thereof, capable of expressing a dsRNA that inhibits a fungal HXT1 gene, comprising transforming a plant cell with an expression cassette or genetic construct according to claim 3.

8. A method of treatment of plants, comprising applying an effective and non-phytotoxic amount of a dsRNA molecule according to claim 1 to soil where plants grow or are capable of growing, to the leaves and/or the fruit of plants or to the seeds of such plants.

9. A method for protecting a plant from infestation by a plant pathogen, comprising applying an effective and non-phytotoxic amount of a dsRNA molecule according to claim 1 to soil where the plant grows or is capable to grow, to the leaves and/or the fruit of such plant or to the seeds of such plant.

10. The method according to claim 9, wherein said plant pathogen is a fungal rust of the order Pucciniales.

11. The method according to claim 10, wherein the fungal rust is: *Phakopsora pachyrhizi, Uromyces fabae, Puccinia striiformis, Puccinia triticina* or *Puccinia graminis.*

12. The method according to claim 11, wherein the fungal rust is *Phakopsora* pachyrhizi.

13. The method according to claim 8, wherein said plant is a soybean plant.

14. A method of treatment of plants, comprising applying an effective and non-phytotoxic amount of a composition according to claim 2 to soil where plants grow or are capable of growing, to the leaves and/or the fruit of plants or to the seeds of such plants.

15. A method for protecting a plant from infestation by a plant pathogen, comprising applying an effective and non-phytotoxic amount of a composition according to claim 2 to soil where the plant grows or is capable to grow, to the leaves and/or the fruit of such plant or to the seeds of such plant.

16. The dsRNA molecule of claim 1, wherein the fungal HXT1 gene is:
a polynucleotide comprising a nucleotide sequence as set forth in SEQ ID NO: 1, or a polynucleotide encoding a polypeptide having an amino acid sequence as set forth in SEQ ID NO: 2.

17. The dsRNA molecule of claim 1, wherein the fungal HXT1 gene is:
a polynucleotide comprising a nucleotide sequence as set forth in SEQ ID NO: 5, or a polynucleotide encoding a polypeptide having an amino acid sequence as set forth in SEQ ID NO: 6.

18. The dsRNA molecule of claim 1, wherein the fungal HXT1 gene is:
a polynucleotide comprising a nucleotide sequence as set forth in SEQ ID NO: 7, or a polynucleotide encoding a polypeptide having an amino acid sequence as set forth in SEQ ID NO: 8.

19. The dsRNA molecule of claim 1, wherein the fungal HXT1 gene is:
a polynucleotide comprising a nucleotide sequence as set forth in SEQ ID NO: 9, or a polynucleotide encoding a polypeptide having an amino acid sequence as set forth in SEQ ID NO: 10.

* * * * *